US010526653B2

(12) United States Patent
Scherer et al.

(10) Patent No.: US 10,526,653 B2
(45) Date of Patent: Jan. 7, 2020

(54) BIOMARKERS FOR AUTISM SPECTRUM DISORDERS

(71) Applicant: The Hospital for Sick Children, Toronto (CA)

(72) Inventors: Stephen W Scherer, Toronto (CA); John B Vincent, Toronto (CA)

(73) Assignees: The Centre for Addiction and Mental Health, Toronto, Ontario (CA); The Hospital for Sick Children, Toronto, Ontario (CA)

(*) Notice: Subject to any disclaimer, the term of this patent is extended or adjusted under 35 U.S.C. 154(b) by 280 days.

(21) Appl. No.: 14/630,205

(22) Filed: Feb. 24, 2015

(65) Prior Publication Data

US 2015/0322518 A1 Nov. 12, 2015

Related U.S. Application Data

(63) Continuation of application No. 12/681,229, filed as application No. PCT/CA2008/001767 on Oct. 3, 2008, now abandoned.

(60) Provisional application No. 61/008,294, filed on Dec. 20, 2007, provisional application No. 60/960,572, filed on Oct. 4, 2007.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

WO WO 2009/043178 4/2009

OTHER PUBLICATIONS

Collins (Proc. Natl. Acad. Sci. U.S.A. 99 (26), 16899-16903 (2002)).*
GenBank record having accession NM_173495, Homo sapiens patched domain containing 1 (PTCHD1, mRNA), Sep. 6, 2006, 2 pages.*
Onat, Jul. 2006, Thesis: In Silico Identification of Candidate MECP2 targets and Quantitative Analysis in Rett Syndrome, 112 pages.*
Schaefer et al. (1993, Nature Genetics, vol. 4, pp. 272-279).*
Durand et al. Nature Genetics, vol. 39, No. 1, pp. 25-27, 2007.
Durand C.M. et al., "Mutations in the gene encoding the synaptic scaffolding protein SHANK3 are associated wiht autism spectrum disorders," Nature Genetics Supplementary Information [online]; Dec. 2006, Macmillan Publishers Limited, London, UK, [Retrieved on Sep. 8, 2015]. Retrieved from the INternet: <URL:http://www.nature.com/ng/journal/v39/n1/suppinfo/ng1933?S1.html>.
Jamain, et al. Mutations of the X-linked genes encoding neuroligins NLGN3 and NLGN4 are associated with autism. Nat Genet. May 2003; 24(1): 27-29.
Feng, et al. High frequency of neurexin 1beta signal peptide structural variants in patients with autism. Neuroscience Letters 409 (2006) 10-13.
Sebat, et al. Strong Association of De Novo Copy Number Mutations with Autism. Science 2007; 316 (5823): 445-9.
Szatmari, et al. Mapping autism risk loci using genetic linkage and chromosomal rearrangements. Nature Genetics vol. 39, No. 3 Mar. 2007, 319-328.
Jacquemont et al. Array-based comparative genomic hybridisation identifies high frequency of cryptic chromosomal rearrangements in patients with syndromic autism spectrum disorders. J Med Genet 2006;43:843-849.
Moessner et al. Contribution of SHANK3 Mutations to Autism Spectrum Disorder. The American Journal of Human Genetics, vol. 81, Dec. 2007, p. 1289-1297.
Durand, et al. Mutations in the gene encoding the synaptic scaffolding protein SHANK3 are associated with autism spectrum disorders. Nat Genet. Jan. 2007 ; 39(1): 25-27.
Marshall, et al. Structural Variation of Chromosomes in Autism Spectrum Disorder. The American Journal of Human Genetics 82, 477-488, Feb. 2008 477-488.
Jeffries et al. (American Journal of Medical Genetics 137A: 139-147 (2005)).
Anderlid et al. (Hum Genet (2002) 110:439-443).
Bonaglia et al. (Americal Journal of Human Genetics (69:261-268, 2001).
Manning et al. Pediatrics, vol. 114, No. 2, Aug. 2004.
Wilson et al. Journal of Medical Genetics, 2003; 40: 575-584.
Luciani et al. J Med Genet 2003; 40:690-696.

* cited by examiner

*Primary Examiner* — Juliet C Switzer
(74) *Attorney, Agent, or Firm* — Gowling WLG (Canada) LLP

(57) ABSTRACT

Methods of determining the risk of ASD in an individual are provided which comprise identifying the presence of one or more genomic mutations in one or more of the genes, PTCHD1, SHANK3, NFIA, DPP6, DPP10, DYPD, GPR98, PQBP1, ZNF41 and FTSJ1.

3 Claims, 10 Drawing Sheets

Specification includes a Sequence Listing.

```
GCTCTAGGAT GCTGCGGCAG GTTCTGCACA GGGGCTTGAG GACGTGTTTC  50
TCCCGGCTCG GCCACTTCAT TGCCAGTCAC CCTGTCTTCT TCGCCTCGGC  100
GCCGGTGCTC ATCTCCATCC TGCTCGGCGC CAGCTTCAGC CGCTACCAGG  150
TCGAGGAGAG CGTGGAGCAC CTGCTGGCGC CCAGCACAG  CCTGGCCAAG  200
ATCGAGCGCA ACCTCGTTAA CAGCCTCTTC CCGGTCAACC GCTCCAAGCA  250
CCGTCTCTAC TCGGACCTGC AGACCCCGG  GCGCTACGGC CGGGTCATCG  300
TCACCTCCTT CCAGAAAGCC AACATGCTGG ACCAGCATCA CACCGACCTG  350
ATCTTAAAGT TGCATGCTGC TGTCACCAAG ATCCAGGTTC CAAGGCCTGG  400
TTTTAATTAC ACGTTTGCCC ATATATGTAT CCTGAATAAT GATAAGACTT  450
GCATCGTGGA TGACATAGTG CACGTCCTGG AAGAGCTAAA GAATGCTCGG  500
GCCACCAATC GGACCAATTT TGCTATCACA TACCCAATCA CTCACTTAAA  550
GGACGGGAGG GCTGTGTACA ATGGGCACCA GCTTGGGGGC GTCACTGTGC  600
ACAGCAAAGA CCGGGTGAAA TCTGCAGAGG CCATCCAGCT CACCTACTAC  650
CTGCAGTCAA TCAACAGTCT CAATGACATG GTGGCTGAGA GGTGGGAGTC  700
CAGCTTCTGC GACACTGTCA GACTGTTTCA GAAATCCAAC AGCAAAGTCA  750
AAATGTACCC TTACACGTCC TCCTCACTGA GGGAAGATTT CCAGAAGACC  800
AGCCGCGTAT CAGAACGTTA CCTGGTCACC AGCCTGATTC TGGTGGTTAC  850
CATGGCCATC CTGTGTTGCT CTATGCAGGA CTGCGTCCGC AGCAAACCCT  900
GGCTAGGCCT GCTCGGATTG GTGACCATAA GCCTGGCCAC TCTCACTGCA  950
GCCGGGATCA TCAATCTTAC TGGTGGGAAA TATAATTCCA CCTTCCTGGG  1000
AGTCCCTTTC GTCATGCTAG GTCATGGATT ATATGGGACT TTTGAAATGT  1050
TATCCTCCTG GAGGAAAACT AGAGAAGACC AACATGTTAA AGAGAGAACT  1100
GCAGCAGTCT ATGCAGACTC CATGCTCTCC TTTTCTCTCA CCACTGCCAT  1150
GTACCTGGTC ACCTTTGGCA TAGGGGCCAG CCCTTTCACG AACATTGAGG  1200
CAGCCAGGAT TTTCTGCTGC AATTCCTGTA TTGCAATCTT CTTCAACTAC  1250
CTCTATGTAC TCTCGTTTTA TGGTTCCAGC CTAGTGTTCA CTGGCTACAT  1300
AGAAAACAAT TACCAGCATA GTATCTTCTG TAGAAAAGTC CCAAAGCCTG  1350
AGGCATTGCA GGAGAAGCCG GCATGGTACA GGTTCTCCT  GACGGCCAGA  1400
TTCAGTGAGG ACACAGCTGA AGGCGAGGAA GCGAACACTT ACGAGAGTCA  1450
CCTATTGGTA TGTTTCCTCA AACGCTATTA CTGTGACTGG ATAACCAACA  1500
CCTATGTCAA GCCTTTTGTA GTTCTCTTTT ACCTTATTTA TATTTCCTTT  1550
GCCTTAATGG GCTATCTGCA GGTCAGTGAA GGGTCAGACC TTAGTAACAT  1600
TGTAGCAACC GCGACACAAA CCATTGAGTA CACTACTGCC CAGCAAAAGT  1650
ACTTCAGCAA CTACAGTCCT GTGATTGGGT TTTACATATA TGAGTCTATA  1700
GAATACTGGA ACACTAGTGT CCAAGAAGAT GTTCTAGAAT ACACCAAGGG  1750
GTTTGTGCGG ATATCCTGGT TTGAGAGCTA TTTAAATTAC CTTCGGAAAC  1800
TCAATGTATC CACTGGCTTG CCTAAGAAAA ATTTCACAGA CATGTTGAGG  1850
AATTCCTTTC TGAAAGCCCC TCAATTTTCA CATTTTCAAG AGGACATCAT  1900
CTTCTCTAAA AAATACAATG ATGAGGTCGA TGTAGTGGCC TCCAGAATGT  1950
TTTTGGTGGC CAAGACCATG GAAACAAACA GAGAAGAACT CTATGATCTC  2000
TTGGAAACCC TGAGGAGACT TTCTGTCACC TCCAAGGTGA AGTTCATCGT  2050
CTTCAATCCG TCCTTTGTAT ACATGGATCG ATATGCCTCC TCTCTGGGAG  2100
CCCCCCTGCA CAACTCCTGC ATCAGTGCTT TGTTCCTGCT CTTCTTCTCG  2150
GCATTCCTGG TGGCAGATTC ACTGATTAAC GTCTGGATCA CTCTCACAGT  2200
TGTGTCCGTG GAGTTTGGAG TGATAGGTTT CATGACATTA TGGAAAGTAG  2250
AACTGGACTG CATTTCTGTG CTATGCTTAA TTTATGGAAT TAATTACACA  2300
ATTGACAATT GTGCTCCAAT GTTATCCACA TTTGTTCTGG CAAGGATTT   2350
CACAAGAACT AAATGGGTAA AAAATGCCCT GGAAGTGCAT GGGGTAGCTA  2400
TTTTACAGAG TTACCTCTGC TATATTGTTG GTCTGATTCC TCTTGCAGCT  2450
GTGCCTTCAA ATCTGACCTG TACACTGTTC AGGTGCTTGT TTTTAATAGC  2500
ATTTGTCACC TTCTTTCACT GCTTTGCCAT TTTACCTGTG ATACTGACTT  2550
TCCTGCCACC CTCTAAGAAA AAAAGGAAAG AGAAGAAAA  TCCTGAGAAC  2600
CGGGAGGAAA TTGAGTGTGT AGAAATGGTA GATATCGATA GTACCCGTGT  2650
GGTTGACCAA ATTACAACAG TGTGATAATG TCTGCTTGGC ATATTTTCAC  2700
```

Figure 7A1

```
CTTAGGTCTT ATCAAGACCA AAGAGATTAT GTTAATGAAA CAATTAAATT  2750
CAAAGTTCTT CCCTTTTTTA AAGATAGGAA ACAGGCATTG CCAAAAAAAA  2800
AAAAAAAAAA AAAAGGAAAG GACAGTGGGG AGAAATGGGC CTGGCATATT  2850
TTCAGTCTTT AAAACAAAGG AGTTGTTATG AGAATTCACA CACACATAGA  2900
CACACACACA CACACACACA CACACACACA CACACACACA CCCTGGGAGA  2950
CCTATAGTCT CTTAAACTAA GATCAAGTAG AAGAAAGCTT ATTAACAAGC  3000
AGGATCCTGC CTTATCCAAA CTGCAGATGT TGCTGGCATT GTGACAAAAC  3050
CCACTGATTG AAAGGTCAAC TGCCAAGGCA GAAACACCTT TAAGCATTGT  3100
TCAAACAATA AGGCTTCCAG AACTTCTGTA GAGCAGTAGC TCCAGTCATG  3150
GTCTGTGGTT TGAGGTTTTA GCTGTCTCAC CTAGCTCCCT AACACTGAAG  3200
GAGATACTTG TGAAAGTTCT GACCAGCAAA AGCAAGCCAG AGCCTTGGAA  3250
ACTGATATGT GGTAGAGTGG CCATCACTCA TGGACTAAAA TTGATTCACC  3300
GCTAAATTTA CCCAGGTGAA GCAGTTTCGT TGTCTAGAAT GAAATTATCA  3350
TATTCCGCCA TTGGTATGCC TTTAACATTT GTATAGTTTG GTTGCTTAA   3400
AACACCTTAA AACCAATGAC AGCTCCAGCA CTGCAGAATT GGTGTGATTC  3450
TACTTTGGAA TAGCTTGTCA CTTGTCACCA AATGGGTCTG CTTTATTAGT  3500
TACAGCTCTT GGCAGGAGGA TCCAGGGACC CAAAACCACA GGGCCAAACC  3550
CAAATACCTG GCATGATGGA GCAAAAGCAG GTGTCTACTT GGACCCAGAT  3600
ATAGTGTCTC CATTTTAACA ACAACAACAA AATAGCCAGC TGGTACAGCT  3650
GTTTGCATTG GCCCTACATG CATTTTTGC ATGGATATCC AGAAACATCT   3700
GCCCACACAA AACTGCGGGG AAAAAAAATG AACACTGAAA TAGTTATTTG  3750
CTGTTGCTTC CAACTTGTAG TGCCAGTCTG CCTTTGCTGT GAAACACACC  3800
TGCTCAGAGA CAGAGAGGGG AAGAAGATCT TTGGTAAGTC TAAGTCCTGA  3850
CGCTGAGAAG CTTTGTAAAA GTGCAGGGAG ATAAAGGGCC AAAAGGGAGA  3900
TAGATGGAAA ACACTGGAAA AAGTATTCAC TGATACAAAT CTATCAATGA  3950
TGGCAGTCCA ATTCTCTTGC TAAAGTGGCT GCACCTCACC TTGCTGGTCC  4000
CCCCCACACC TTTTTTGATG TCCTTCTGCG TCATCATAGC AAGGCCCTTC  4050
TGTAAATTAA CAAGCCTAGA TATTTATACT CTTGACTTCC AGTATCTACA  4100
GAAGAATGGT TCATAGATCT AAACAGAAAT GGTTTAGATC TAAAAAGGCT  4150
GTATACGTTG CCCAGGCCCC TGCATTTCTT TAAATTTATA AAAATGAAGC  4200
TAAAACCTGG TTACATTTGA AGCAAATATC TACAGTATTT TTCCCTTTTA  4250
GAGATGTAGC TTCCTTAGAC ATCTGTAGTG GTAAGCATTT CCCAAAAGCA  4300
TCTTACCTTT CTGAACCTTA GCAGACATAC TGTGCAGCTT ACCTATCTTC  4350
TGCAGAGGAG GAAACTGAGA CCTAGGAGAA TAAAGTGACT CACTCAGGTC  4400
ACACCACTAA AGGGTTTTCA TCATTTCAGC ATACCTAAGA CAGGGCAGTC  4450
CAATTTTCAG TATTCTCATA AGATGGCTAT TACTCCTCTC AAAATGCATT  4500
TCCAAAGTAG GAACATAGGA CTTCGTTGGC CACAGGGCAG ACATTTTTTT  4550
AGTGTCTGGA ATTAAAATGT TTGAGGTTTA GGTTTGCCAT TGTCTTTCCA  4600
AAAGGCCAAA TAATTCAGAT GTAACCACAC CAAGTGCAAA CCTGTGCTTT  4650
CTATTTCACG TACTGTTGTC CATACAGTTC TAAATACATG TGCAGGGGAT  4700
TGTAGCTAAT GCATTACACA GTCGTTCAGT CTTCTCTGCA GACACACTAA  4750
GTGATCATAC CAACGTGTTA TACACTCAAC TAGAAGATAA TAAGCTTTAA  4800
TCTGAGGGCA AGTACAGTCC TGACAAAAGG GCAAGTTTGC ATAATAGATC  4850
TTCGATCAAT TCTCTCTCCA AGGGGCCCGC AACTAGGCTA TTATTCATAA  4900
AACACAACTG AAGAGGGGAT TGGTTTTACT GTTAAATCAT GTGTTGCTAA  4950
ATCATTTTCT GAACAGTGTG TTCTAAATCA GTCATTGATT TAGTGTCAGC  5000
CACGTGGAGC ACCTCGGCTT AAAGCAGCTC CACAAACCT GACACAACAC   5050
ACACACCAAT TAAATGGATT TTGTTGAGAA TTAATCATT CAATTTGGTC    5100
AACCAGAATG ACTTCCTGTA GAACTCTGTT TTATGACAGA TAATAGTTTT  5150
CCAACTTGAT TGAGTCTCTG TATACCCTGG GATATTGTAT TTTTTAATGA  5200
AGGGCATTTT CAAACTTGTC AACTTCTCTT TTCAGCACTT GAAATGAAGG  5250
CTTATGGAAT TCTGACTGTG AAATGAATTT TTCTATTGGG AAAAAAAAAA  5300
AAAAA    (SEQ ID NO: 17)
```

Figure 7A2

MLRQVLHRGLRTCFSRLGHFIASHPVFFASAPVLISILLGASFSRYQVEE
SVEHLLAPQHSLAKIERNLVNSLFPVNRSKHRLYSDLQTPGRYGRVIVTS
FQKANMLDQHHTDLILKLHAAVTKIQVPRPGFNYTFAHICILNNDKTCIV
DDIVHVLEELKNARATNRTNFAITYPITHLKDGRAVYNGHQLGGVTVHSK
DRVKSAEAIQLTYYLQSINSLNDMVAERWESSFCDTVRLFQKSNSKVKMY
PYTSSSLREDFQKTSRVSERYLVTSLILVVTMAILCCSMQDCVRSKPWLG
LLGLVTISLATLTAAGIINLTGGKYNSTFLGVPFVMLGHGLYGTFEMLSS
WRKTREDQHVKERTAAVYADSMLSFSLTTAMYLVTFGIGASPFTNIEAAR
IFCCNSCIAIFFNYLYVLSFYGSSLVFTGYIENNYQHSIFCRKVPKPEAL
QEKPAWYRFLLTARFSEDTAEGEEANTYESHLLVCFLKRYYCDWITNTYV
KPFVVLFYLIYISFALMGYLQVSEGSDLSNIVATATQTIEYTTAQQKYFS
NYSPVIGFYIYESIEYWNTSVQEDVLEYTKGFVRISWFESYLNYLRKLNV
STGLPKKNFTDMLRNSFLKAPQFSHFQEDIIFSKKYNDEVDVVASRMFLV
AKTMETNREELYDLLETLRRLSVTSKVKFIVFNPSFVYMDRYASSLGAPL
HNSCISALFLLFFSAFLVADSLINVWITLTVVSVEFGVIGFMTLWKVELD
CISVLCLIYGINYTIDNCAPMLSTFVLGKDFTRTKWVKNALEVHGVAILQ
SYLCYIVGLIPLAAVPSNLTCTLFRCLFLIAFVTFFHCFAILPVILTFLP
PSKKKRKEKKNPENREEIECVEMVDIDSTRVVDQITTV (SEQ ID NO: 18)

Figure 7B

BIOMARKERS FOR AUTISM SPECTRUM DISORDERS

FIELD OF THE INVENTION

The present invention relates to genetic markers for Autism Spectrum Disorders (ASD).

BACKGROUND OF THE INVENTION

Autism is a heritable neurodevelopmental condition characterized by impairments in social communication and by a preference for repetitive activities. Autism is not a distinct categorical disorder but is the prototype of a group of conditions defined as Pervasive Developmental Disorders (PDDs) or Autism Spectrum Disorders (ASD), which include Asperger's Disorder, Childhood Disintegrative Disorder, Pervasive developmental disorder—not otherwise specified (PDD-NOS) and Rett Syndrome. ASD is diagnosed in families of all racial, ethnic and social-economic backgrounds with incidence roughly four times higher in males compared to females. Overall population prevalence of autism has increased in recent years to a current estimate of 20 in 10,000 with incidence as high as 60 in 10,000 for all autism spectrum disorders.

Data from several epidemiological twin and family studies provide substantial evidence that autism has a significant and complex genetic etiology. The concordance rate in monozygotic twins is 60-90% (Bailey 1995), and the recurrence rate in siblings of affected probands has been reported to be between 5-10% (Jones & Szatmari 1988) representing a 50 fold increase in risk compared to the general population. Although autism spectrum disorders are among the most heritable complex disorders, the genetic risk is clearly not conferred in simple Mendelian fashion.

In a minority of cases (~10%), autism is part of a broader recognizable disorder (e.g. fragile X syndrome, tuberous sclerosis) or is associated with cytogenetically-detectable chromosome abnormalities. Moreover, co-morbidity of autism with microdeletion syndromes (e.g. William-Beuren and Sotos) and other genomic disorders (e.g. Prader-Willi/Angelman) suggests chromosomal imbalances are involved in the underlying etiology. The most frequent cytogenetic anomaly is an interstitial, maternally-inherited duplication of 15q11-13 (1-3%) encompassing the Prader Willi/Angelman Syndrome critical region. There are also a large number of cases with deletions in the q11.2 and q13.3 regions of chromosome 22. The 22q11.2 region is associated with velo-cardio-facial Syndrome and deletions at 22q13.3 appear to also represent a clinically definable syndrome. Both deletions are associated with the autistic phenotypes. Other chromosome loci associated with anomalies with a higher frequency of events observed in syndromic forms of ASD include 7q (see TCAG www.chr7.org), 2q37, 5p14-15, 17p112. In addition, reciprocal duplications overlapping the William-Beuren deletion region have been associated with the autism phenotype.

Genome-wide linkage scans have found evidence for susceptibility loci on almost all chromosomes with 7q yielding the most consistent results. Other loci with significant linkage include 2q (IMGSAC 2001), 3q and most recently 11p (AGP 10K study). In some instances, like 7q, there is considerable overlap between cytogenetic anomalies and linkage results. However, the lack of linkage found at 15q11-13 and 22q13.3 loci reflect considerable heterogeneity in ASD and suggest that these rearrangements are responsible for a particular ASD subtype involving genes that do not contribute to the phenotype in cytogenetically normal patients. Despite promising results, no specific genes within these linkage peaks have unequivocally been shown to contribute to autism.

Mutations associated with ASD have been reported in two neuroligin (NLGN3 and NLGN4) genes and more recently SHANK3; however, these account for only rare causes of ASD. Other genes have been implicated, but represent rare events or have not yet been validated by other studies.

Together these data suggest substantial genetic heterogeneity with the most likely cause of non-syndromic idiopathic ASD involving multiple epistatically-interacting loci.

The identification of large scale copy number variants (CNVs) represents a considerable source of genetic variation in the human genome that contributes to phenotypic variation and disease susceptibility found small inherited deletions in autistic kindreds suggesting possible susceptibility loci.

It would be desirable to identify genetic markers of ASD that facilitate in a determination of the risk of ASD in an individual, as well as to assist in the diagnosis of the condition.

SUMMARY OF THE INVENTION

A number of genetic markers have now been identified which are useful in assessing the risk of ASD in an individual, as well as being useful to diagnose the condition. The markers are useful both individually and in the form of a microarray to screen individuals for risk of ASD.

Thus, in one aspect of the present invention, a method of determining the risk of ASD in an individual is provided comprising:

probing a nucleic acid-containing sample obtained from the individual for a gene encoding PTCHD1, wherein a determination that the gene comprises a deletion of at least a portion of exon 1 is indicative of a risk of ASD in the individual.

In another aspect of the present invention, a method of determining the risk of ASD in an individual is provided comprising:

probing a nucleic acid-containing sample obtained from the individual for a mutation that modulates the expression of at least one gene selected from the group consisting of PTCHD1, SHANK3, NFIA, DPP6, DPP10, GPR98, PQBP1, ZNF41 and FTSJ1, wherein identification of a mutation that modulates the expression of at least one of said genes is indicative of a risk of ASD.

In another aspect of the invention, a method of determining the risk of ASD in an individual is provided comprising:

screening a biological sample obtained from the individual for abnormal levels of at least one gene product expressed by a gene selected from the group consisting of PTCHD1, SHANK3, NFIA, DPP6, DPP10, GPR98, PQBP1, ZNF41 and FTSJ1, wherein a determination that at least one of said gene products is expressed at a level that varies from the level in a healthy non-ASD individual is indicative of a risk of ASD.

In a further aspect of the invention, a method of determining the risk of ASD in an individual is provided comprising:

screening a nucleic acid-containing sample from the individual for genomic sequence variations that modulate the expression of PTCHD1.

These and other aspects of the present invention are described by reference to the following figures in which:

BRIEF DESCRIPTION OF THE DRAWINGS

FIG. 7 illustrates the cDNA sequence (A1 and A2) of the PTCHD1 gene and the corresponding amino acid sequence (B)

DETAILED DESCRIPTION OF THE INVENTION

Figure 1:
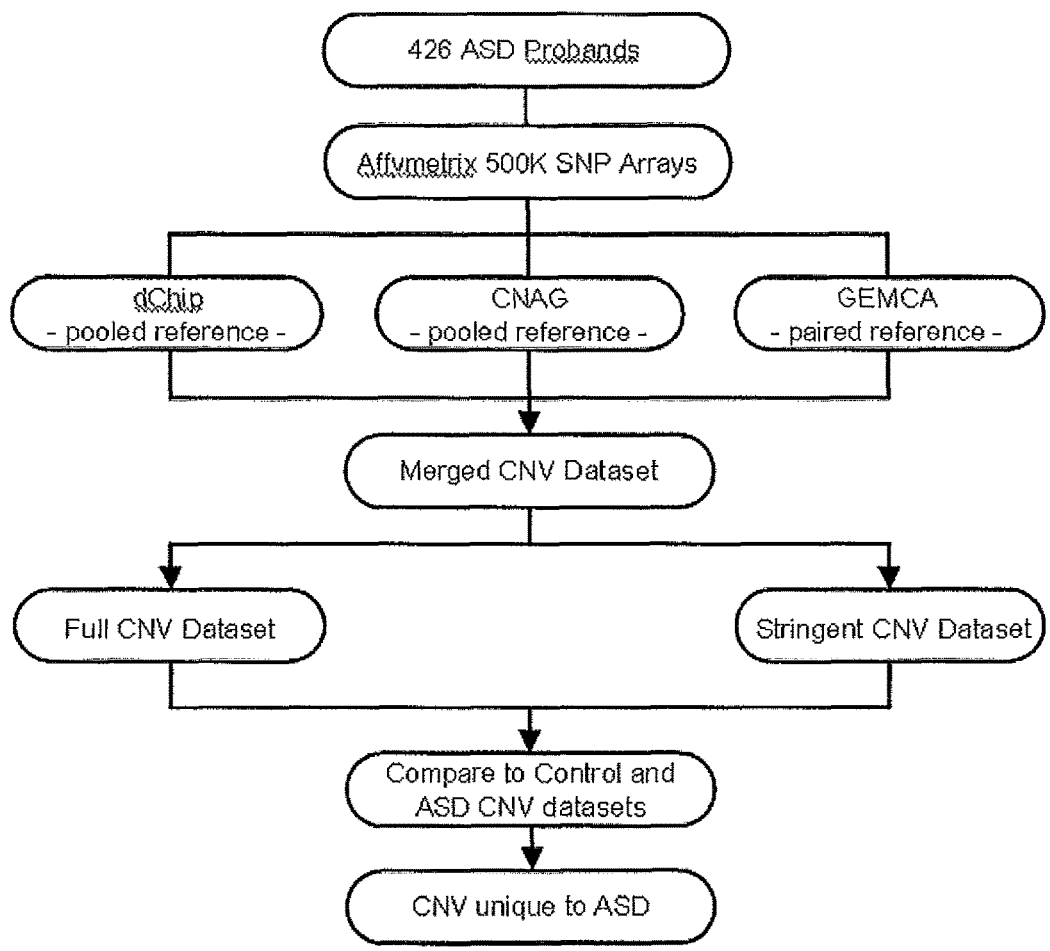
FIG. 1 is a flow chart depicting the methodology used to identify ASD-specific CNVs.

A method of determining the risk of an autism spectrum disorder (ASD) in an individual is provided comprising screening a biological sample obtained from the individual for a mutation that may modulate the expression of at least one gene selected from the group consisting of PTCHD1, SHANK3, NFIA, DPP6, DPP10, DPYD, GPR98, PQBP1, ZNF41 and FTSJ1. Such genes are referred to herein as "ASD-associated" genes.

The term "an autism spectrum disorder" or "an ASD" is used herein to refer to at least one condition that results in developmental delay of an individual such as autism, Asperger's Disorder, Childhood Disintegrative Disorder, Pervasive Developmental Disorder—Not Otherwise Specified (PDD-NOS) and Rett Syndrome (APA DSM-IV 2000).

In the present method of determining ASD risk in an individual, a biological sample obtained from the individual is utilized. A suitable biological sample may include, for example, a nucleic acid-containing sample or a protein-containing sample. Examples of suitable biological samples include saliva, urine, semen, other bodily fluids or secretions, epithelial cells, cheek cells, hair and the like. Although such non-invasively obtained biological samples are preferred for use in the present method, one of skill in the art will appreciate that invasively-obtained biological samples, may also be used in the method, including for example, blood, serum, bone marrow, cerebrospinal fluid (CSF) and tissue biopsies such as tissue from the cerebellum, spinal cord, prostate, stomach, uterus, small intestine and mammary gland samples. Techniques for the invasive process of obtaining such samples are known to those of skill in the art. The present method may also be utilized in prenatal testing for the risk of ASD using an appropriate biological sample such as amniotic fluid and chorionic villus.

In one aspect, the biological sample is screened for nucleic acid encoding selected genes in order to detect mutations associated with an ASD. It may be necessary, or preferable, to extract the nucleic acid from the biological sample prior to screening the sample. Methods of nucleic acid extraction are well-known to those of skill in the art and include chemical extraction techniques utilizing phenol-chloroform (Sambrook et al., 1989), guanidine-containing solutions, or CTAB-containing buffers. As well, as a matter of convenience, commercial DNA extraction kits are also widely available from laboratory reagent supply companies, including for example, the QIAamp DNA Blood Minikit available from QIAGEN (Chatsworth, Calif.), or the Extract-N-Amp blood kit available from Sigma (St. Louis, Mo.).

Once an appropriate nucleic acid sample is obtained, it is subjected to well-established methods of screening, such as those described in the specific examples that follow, to detect genetic mutations indicative of ASD, i.e. ASD-linked mutations. Mutations, such as genomic copy number variations (CNVs), which include gains and deletions of segments of DNA, for example, segments of DNA greater than about 1 kb, such as DNA segments between about 300 and 500 kb, as well as base pair mutations such as nonsense, missense and splice site mutations, including sequence mutations in both coding and regulatory regions of a gene, have been found to be indicative of ASD.

ASD-linked mutations such as CNVs are not restricted to a single chromosome, but rather have been detected on a multiple chromosomes such as the X chromosome, chromosome 15 and chromosome 21, and on various regions of the same chromosome such as at Xp11 and Xp22. Examples of CNVs that have been determined to be linked to ASD include a deletion on chromosome Xp22 including at least a portion of exon 1 of the PTCHD1 gene; a duplication on chromosome 15q11; and a deletion within the SHANK3 gene.

Genomic sequence variations of various types in different genes have been identified as indicative of ASD. CNVs in the DPP10 gene, including intronic gains, such as a 105 kb intronic gain, and exonic losses, such as a 478 kb exonic loss, both of which are more specifically identified in Table 1, have been identified; CNVs in the DPP6 gene, such as a 66 kb loss encompassing exons 2 and 3 and gains such as a CNV encompassing the entire DPP6 gene, a 270 kb exonic gain (exon 1), and a 16 kb intronic gain (see Table 1); CNVs in the SHANK3 gene such as a 276 kb loss; and CNVs in the DYPD gene such as a loss of the entire gene.

In one embodiment, genomic sequence variations that inhibit the expression of PTCHD1 have been linked to ASD. The terminology "inhibit expression" refers broadly to sequence variations that may inhibit, or at least reduce, any one of transcription and/or translation, as well as the activity of the PTCHD1 protein. For example, a CNV in the PTCHD1 gene comprising a large deletion of the coding region which results in at least a reduction of the expression of PTCHD1 protein has been found to be indicative of ASD. Although the CNV is not particularly restricted, the CNV deletion may include, for example, at least a portion of exon 1, but may additionally include surrounding regions as well, such as intron 1, in whole or in part, or a portion or more of the upstream region thereof.

Genomic sequence variations other than CNVs have also been found to be indicative of ASD, including, for example, missense mutations which result in amino acid changes in a protein that may also affect protein expression. In one embodiment, missense mutations in the PTCHD1 gene have been identified which are indicative of ASD, including missense mutations resulting in the following amino acid substitutions in the Ptchd1 protein: L73F, I173V, V195I, ML336-337II and E479G.

To determine risk of ASD in an individual, it may be advantageous to screen for multiple genomic mutations, including CNVs and other mutations as indicated above applying array technology. In this regard, genomic sequencing and profiling, using well-established techniques as exemplified herein in the specific examples, may be conducted for an individual to be assessed with respect to ASD risk/diagnosis using a suitable biological sample obtained from the individual. Identification of one or more mutations associated with ASD would be indicative of a risk of ASD, or may be indicative of a diagnosis of ASD. This analysis may be conducted in combination with an evaluation of other characteristics of the individual being assessed, including for example, phenotypic characteristics.

In view of the determination of gene mutations which are linked to ASD, a method for determining risk of ASD in an individual is also provided in which the expression or activity of a product of an ASD-linked gene mutation is determined in a biological protein-containing sample obtained from the individual. Abnormal levels of the gene product or abnormal levels of the activity thereof, i.e. reduced or elevated levels, in comparison with levels that exist in healthy non-ASD individuals, are indicative of a risk of ASD, or may be indicative of ASD. Thus, a determination of the level and/or activity of the gene products of one or more of PTCHD1, SHANK3, NFIA, DPP6, DPP10, DYPD, GPR98, PQBP1, ZNF41 and FTSJ1, may be used to determine the risk of ASD in an individual, or to diagnose ASD.

As one of skill in the art will appreciate, standard assays may be used to identify and quantify the presence and/or activity of a selected gene product.

Embodiments of the invention are described by reference to the following specific examples which is not to be construed as limiting.

Example 1

DNA Samples and Population Structure

The study included 426 ASD families. All of the index cases met Autism Diagnostic Interview-Revised (ADI-R) and Autism Diagnostic Observation Schedule (ADOS) criteria or on a clinical best estimate (Risi et al. J Am Acad Child Adolesc Psychiatry 2006; 45(9):1094-103). Thirty-two of these carried a cytogenetic chromosome rearrangement; 18 were detected by karyotyping 328 of 412 samples that originated from child diagnostic centres at the Hospital for Sick Children in Toronto and from St. John's, Newfoundland; 14 were already known to carry karyotypic anomalies (see Table 1 for information on these 32 patients). Affected and unaffected siblings were also assessed, and 56% (237/426) had one child (simplex) and 44% (189/426) had more than one child (multiplex) with ASD. Most cases were screened for fragile X mutations (75%) and if detected they were not included in the study. Most experiments were performed on blood genomic DNA (80%), otherwise the source was cell lines, e.g. lymphoblast cell lines. Population ancestry was estimated using STRUCTURE (Falush et al. Genetics 2003; 164(4):1567-87; Pritchard et al. Genetics 2000; 155(2):945-59).

TABLE 1

| Sample ID | Phenotype/Family type | Cytogenetic Analysis | | | CNV Analysis | | | | | | |
|---|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| 1 NA0008-000 (50863L) | Simplex family ASD, developmental dyspraxia | 46, XX, t(2; 6)(q32; p22) unknown | 2q33.1: 200,096,682-200,154,790 | SATB2 | 2p11.2 | Loss | 917,200 | 89,056,400-89,973,600 | No/NS | No known genes | NFLD |
| | | | 6p22.3: 21,561,566-21,644,040 | No known genes | 6p21.33 | Gain | 54,600 | 30,134,300-30,188,900 | Yes/NS | ZNRD1, PPP1R11, RNF39, TRIM31 SLC1A2 | |
| | | | | | 11p13 | Gain | 54,200 | 35,332,700-35,386,900 | No/NS | No known genes | |
| | | | | | 13q21.33 | Loss | 28,200 | 69,642,500-69,670,700 | No/NS | No known genes | |
| | | | | | 14q11.2 | Gain | 549,300 | 21,490,300-22,039,600 | No/NS | No known genes | |
| | | | | | 14q32.33 | Loss | 64,000 | 106,152,000-106,216,000 | No/NS | No known genes | |
| 2 NA0005-000 (53601L) | Simplex family ASD, seizure disorder, obesity, macrocephaly | 46, XX, t(4; 5)(q21; q13) unknown | 4q21.3 | Several | 1p13.2 | Gain | 128,963 | 112,783,876-112,912,839 | Yes/NS | ST7L, CAPZA1 | NFLD |
| | | | | | 2q37.3 | Loss | 602,914 Error! Hyperlink reference not valid. | 242,127,468-242,730,382 | No/S | 10 genes | |
| | | | 5q14.2-q14.3: 82,802,678-91,285,973 | Several | 3q29 | Loss | 43,033 | 196,922,636-196,965,669 | No/NS | MUC20, MUC4 | |
| | | | | | 5q15 | Loss | 48,627 | 97,076,449-97,125,076 | No/NS | No known genes | |
| | | | | | 5q21.3 | Loss | 13,000 | 109,391,000-109,404,000 | Yes/NS | No known genes | |
| | | | | | 8p23.1 | Gain | 448,146 | 12,039,387-12,487,533 | No/S | FAM86B1, DEFB130, LOC440053 | |
| | | | | | 14q11.2 | Gain | 223,579 | 19,272,965-19,496,544 | No/S | 6 OR genes | |
| | | | | | 14q11.2 | Gain | 650,430 | 21,407,981-22,058,411 | No/S | No known genes | |
| | | | | | 15q11.2 | Gain | 1,642,961 Error! Hyperlink reference not valid. | 18,446,422-20,089,383 | No/NS | LOC283755, POTE15, OR4M2, OR4N4 | |
| 3 NA0039-000 (69736) | Simplex family ASD, submucous cleft, globally developmentally delayed, large ears, short forehead, | 46, XX, der(22)t(14; 22) (q32; q13) pat inherited | See CNV | See CNV | 9q32 | Gain | 498,000 | 114,038,000-114,536,000 | No/NS | 7 genes | NFLD Unaffected sibling with ADHD has 46, XX, der(14) t(14; 22)(q32; q13) |
| | | | | | 14q32.33 | Gain | 1,436,000 | 104,920,000-106,356,000 | No/NS | 6 genes | |
| | | | | | 15q13.3 | Gain | 502,500 | 29,796,300-30,298,800 | No/NS | CHRNA7 | |

TABLE 1-continued

| Sample ID | Phenotype/Family type | Cytogenetic Analysis Karyotype | Breakpoint Location | RefSeq Genes | Chr | CNV | Size (bp) | Location | AS/Str[a] | RefSeq Genes | Comments |
|---|---|---|---|---|---|---|---|---|---|---|---|
| | distally tapere fingers, severe pes planovalgus | | | | 22q13.31-q31.33 | Loss | 3,231,700 | 46,277,400-49,509,100 | Yes/NS | 40 genes + SHANK3 | SK |
| 4 SK0283-003 (72309) | Simplex family ASD | 47, XX, ring chromosome 1 de novo | See CNV | See CNV | 1p22.3 | Gain | 23,993 | 87,417,351-87,441,344 | Yes/NS | No known genes | |
| | | | | | 1q21.2-q21.3 | Gain | 1,451,926 | 148,095,537-149,547,463 | Yes/S | 36 genes | |
| | | | | | 3p26.1 | Loss | 44,458 | 5,365,506-5,409,964 | Yes/S | No known genes | |
| | | | | | 4p13 | Gain | 95,508 | 44,762,996-44,858,504 | Yes/S | No known genes | |
| | | | | | 4q33 | Loss | 82,224 | 171,715,627-171,797,851 | Yes/NS | No known genes | |
| | | | | | 5q31.3 | Loss | 355,649 | 140,658,658-141,014,307 | Yes/NS | 6 genes | |
| | | | | | 6p12.3 | Gain | 13,950 | 46,962,122-46,976,072 | No/NS | GPR116 | |
| | | | | | 7p14.1 | Loss | 102,939 | 38,041,635-38,144,574 | No/NS | STARD3NL, TARP | |
| | | | | | 7q34 | Loss | 169,191 | 141,813,948-141,983,139 | No/NS | PRSS1 | |
| | | | | | 14q11.2 | Loss | 583,148 | 21,455,546-22,038,694 | No/S | No known genes | |
| | | | | | 15q11.2 | Loss | 1,632,769 | 18,427,103-20,059,872 | No/S | LOC28755, POTE15, OR4M2, OR4N4 KIAA1267 | |
| | | | | | 17q21.31 | Loss | 140,746 | 41,570,665-41,711,411 | No/NS | | |
| 5 SK0044-003 (50067) | Simplex family ASD | 46, XY, t(1; 2)(p22.1; p23)pat der(13; 15)(q10; q10)mat inherited | 1p31.1: 72,065,578-72,163,007 2p24.3: 12,376,807-12,733,637 13q10: in progress 15q10: in progress | NEGR1 No known genes | 7p14.1 | Gain | 85,900 | 39,828,000-39,913,900 | No/NS | CDC2L5 | SK |
| 6 SK0182-003 (52065) | Simplex family ASD | 46 XY, t(1; 9)(q25; p13) inherited | 1q24.2: 167,452,268-167,522,136 9p12: 45,695,701-45,737,008 | No known genes No known genes | 2p24.3 | Gain | 15,100 | 14,304,500-14,319,600 | No/NS | No known genes | SK Younger brother has the same translocation and severe speech and language disorder but does not meet ASD criteria on ADOS. |
| | | | | | 14q11.2 | Gain | 288,100 | 19,204,300-19,492,400 | No/S | 6 genes | |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| 7 SK0335-003 (72815) | Simplex Family ASD, mental retardation | 46, XX, t(2; 10)(q22; q22.3) unknown | 2q23.1: 148,938,284-149,125,547 10q23.31: 91,265,490-91,461,660 | LOC401431, ATP6VOE2 SLC16A12, PANK1, MPHOSPH1 | 2p13.3 | Gain | 374,900 | 70,152,900-70,527,800 | Yes/NS | 6 genes | Others Non-Canadian family |
| | | | | | 3q29 | Gain | 43,033 | 196,922,636-196,965,669 | No/NS | MUC20, MUC4 | |
| | | | | | 5p13.1 | Loss | 272,618 | 38,534,384-38,807,002 | Yes/S | LIFR | |
| | | | | | 6p21.32 | Gain | 162,900 | 32,344,099-32,506,999 | Yes/NS | C6orf10, BTNL2 | |
| | | | | | 8p23.1 | Gain | 21,783 | 12,264,620-12,286,403 | No/NS | No known genes | |
| | | | | | 9q32 | Gain | 22,000 | 114,153,000-114,175,000 | No/S | ORM1, ORM2 | |
| | | | | | 14q11.2 | Gain | 331,503 | 21,717,112-22,048,615 | No/S | No known genes | |
| | | | | | 15q11.2 | Gain | 1,516,085 | 18,427,100-19,943,185 | No/S | LOC283755, POTE15, OR4M2, OR4N4 | |
| | | | | | 16p11.2-11.1 | Gain | 266,336 | 34,325,041-34,591,377 | No/NS | No known genes | |
| | | | | | 17q21.31 | Gain | 201,731 | 41,518,102-41,719,833 | No/S | KIAA1267 | |
| | | | | | 20p12.1 | Loss | 27,500 | 14,973,800-15,001,300 | Yes/S | C20orf133 | |
| 8 SK0126-003 (59144) | Multiplex family ASD | 46, XY, t(2; 11)(p11.2; q13.3) pat inherited | 2p11.2: 89,117,655-89,158,494 11q13.1: 64,821,333-64,861,285 | No known genes POLA2, CDC42EP2, DPF2 | 2q34 | Loss | 3,000 | 213,013,000-213,016,000 | Yes/NS | ERBB4 | Other Canadian Family |
| 9 SK0152-003 (41548L) | Multiplex family ASD, oral motor apraxia, poor balance and coordination, mild hypotonia, walks with a wide gait, severe language delay, moderate intellectual disability, some facial features of Cri du Chat | 46, XY, inv(3)(p24; q24), t(5; 7)(p15p13) de novo | 3p24: not available 3q24: not available 5p14.3: 19,825,926-19,883,410 7p13: 46,618,434-46,733,542 | CDH18 No known genes | 3p25.1-p24.3 | Loss | 1,409,600 | 15,125,800-16,535,400 | Yes/S | 12 genes | Other Canadian Family Previously described in a manuscript by Harvard et al[1]. The 3p25.1, 5p15.31-p15.2 and 18q12.2 deletions were identified in Harvard, C. et al using BAC CGH. The deletion size has been refined here using SNPs. Older sibling also |
| | | | | | 3p12.3 | Gain | 55,000 | 78,902,000-78,957,000 | Yes/S | ROBO1 | |
| | | | | | 5p15.31-p15.2 | Loss | 3,429,389 | 9,275,811-12,705,200 | Yes/S | 8 genes | |
| | | | | | 6q16.1 | Loss | 60,058 | 95,556,287-95,616,345 | No/S | No known genes | |
| | | | | | 7p14.1 | Gain | 35,243 | 38,096,725-38,131,968 | No/NS | No known genes | |
| | | | | | 10q11.22 | Gain | 455,130 | 47,030,119-47,485,249 | No/S | ANXA8 | |
| | | | | | 12p11.21 | Gain | 63,728 | 31,904,362-31,968,090 | No/S | No known genes | |
| | | | | | 12q12 | Loss | 422,842 | 40,584,198-41,007,040 | Yes/S | YAF2, ZCRB1 | |

TABLE 1-continued

| Sample ID | Phenotype/Family type | Cytogenetic Analysis Karyotype | Breakpoint Location | RefSeq Genes | CNV Analysis Chr | CNV | Size (bp) | Location | AS/Str[a] | RefSeq Genes | Comments |
|---|---|---|---|---|---|---|---|---|---|---|---|
| | | | | | 14q11.2 | Gain | 491,397 | 21,584,229-22,075,626 | No/S | No known genes | has ASD but has a normal 46, XX karyotype |
| | | | | | 14q32.33 | Gain | 22,269 | 106,223,861-106,246,130 | No/NS | No known genes | Maternal aunt with schizophrenia and a maternal uncle with Down syndrome |
| | | | | | 15q11.2 | Loss | 1,632,718 | 18,446,422-20,079,140 | No/S | LOC283755, POTE15, OR4M2, OR4N4 | |
| | | | | | 16q21 | Loss | 91,432 | 63,768,909-63,860,341 | Yes/NS | No known genes | |
| | | | | | 17q21.31 | Gain | 219,797 | 41,500,036-41,719,833 | No/NS | KIAA1267 | |
| | | | | | 18q12.2 | Loss | 816,914 | 32,174,061-32,990,975 | Yes/S | KIAA1328, C18orf10, FHOD3 | |
| 10 SK0105-003 (27155L) | Multiplex family ASD, primarily non-verbal, profound developmental delay | 46, XY, inv(4)(p12; p15.3)mat inherited | 4p15.3: 12,173,445-12,335,572 | No known genes | 10q11.21 | Gain | 1,098,400 | 41,956,500-43,054,900 | Yes/NS | RET, RASGEF1A, BMS1L, ZNF11B, MGC16291, GALNACT-2 | SK Described previously in Vincent et al.[2] Affected brother, apparently unaffected mother and unaffected maternal grandfather all have the same inversion. Distal 4p15.3 breakpoint maps ~12 Mb to a region previously indicated to show linkage to autism. |
| | | | 4p12: 44,876,353-46,024,486 | GABRG1 (breakpoint region is located in intron 7) | 13q14.2 | Gain | 162,300 | 47,414,800-47,577,100 | Yes/NS | MED4, NUDT15, SUCLA2 | |
| | | | | | 16q21 | Loss | 56,600 | 61,854,900-61,911,500 | Yes/NS | No known genes | |
| | | | | | 17q21.31 | Gain | 238,600 | 41,521,600-41,760,200 | No/NS | KIAA1267 | |
| 11 SK0205-004 (56242) | Simplex ASD | 46, XX, del(5)(p15.1) de novo | See CNV | See CNV | 3q29 | Gain | 96,068 | 199,226,000-199,322,068 | No/NS | LMLN, LOC348840 | SK FISH analysis with subtelomeric probe (containing D5S2488) was consistent with a terminal deletion on 5p. |
| | | | | | 5p15.33-p15.2 | Loss | 13,800,984 | 81,949-13,882,933 | Yes/S | >50 genes | |
| | | | | | 5q15 | Loss | 70,891 | 97,054,185-97,125,076 | No/NS | No known genes | |
| | | | | | 10q11.22 | Gain | 1,121,866 | 46,363,383-47,485,249 | No/S | SYT15, ANXA8, ANXA8L1, PPYR1, GPRIN2 | |
| | | | | | 10q21.3 | Loss | 29,732 | 67,747,770-67,777,502 | No/NS | CTNNA3 | |
| | | | | | 10q26.3 | Gain | 244,432 | 135,079,000-135,323,432 | No/S | SYCE1; CYP2E1 | |
| | | | | | 14q11.2 | Gain | 217,035 | 19,272,965-19,490,000 | No/S | OR4K1, OR4N2, OR4K5, OR4K2 | |

TABLE 1-continued

| Sample ID | Phenotype/Family type | Cytogenetic Analysis | | | CNV Analysis | | | | | | |
|---|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| 12 SK0061-003 (44951) | Simplex family ASD, developmental delay | 46, XY, t(5; 7)(q15; q31.32) unknown | 7q31.31: 118,928,065-119,006,076 | No known genes | 15q11.2 | Gain | 1,662,300 | 18,427,100-20,089,400 | No/NS | LOC28755, POTE15, OR4M2, OR4N4 | Other Non-Canadian Family |
| | | | 5q14.3: 88,849,193-88,891,151 | No known genes | 17q21.31 | Gain | 65,845 | 41,006,823-41,072,668 | No/S | No known genes | |
| | | | | | 17q21.31 | Gain | 187,028 | 41,521,621-41,708,649 | No/NS | KIAA1267 | |
| | | | | | 22q11.21 | Gain | 150,753 | 17,265,500-17,416,253 | No/S | DGCR6, PRODH, DGCR2 | |
| 13 SK0195-003 (55310) | Simplex family ASD | 46, XY, t(5; 8; 17)(q31.1; q24.1; q21.3) de novo | 5q31.1: 136,979,583-137,038,092 | KLHL3 | | | | No CNV detected | | | Other Canadian Family |
| | | | 8q24.22: 132,448,049-132,512,973 | No known genes | 2p16.1 | Gain | 47,900 | 57,314,000-57,361,900 | No/NS | No known genes | |
| | | | 17q21.31: 41,893,216-42,093,636 | LRRC37A2, ARL17P1, LOC641522, NSF | 10q23.1 | Loss | 17,500 | 83,772,000-83,789,500 | Yes/NS | NRG | |
| | | | | | 14q11.2 | Gain | 288,100 | 19,204,300-19,492,400 | No/NS | OR4K1, OR4N2, OR4M1, OR4K5, OR4Q3, OR4K2 | |
| | | | | | 17q21.31 | Gain | 644,700 | 41,521,600-42,166,300 | No/S | KIAA1267 | |
| 14 SK0133-003 (46012) | Simplex family ASD | 46, XY, t(6; 7)(p11.2; q22)pat inherited | 6p12.1: 56,805,919-56,967,398 | DST, c6orf65 | 2q37.1 | Gain | 314,000 | 232,076,000-232,390,000 | Yes/NS | MGC43122, NMUR1, MGC35154, NCL, B3GNT7 | Other Canadian Family CNV seen at 11q25 is in the same breakpoint region as Sample SK0145-003 |
| | | | 7q22.1: 97,933,646-97,973,368 | No known genes | 5q14.3 | Gain | 633,400 | 89,492,800-90,126,200 | Yes/NS | CETN3, LOC153364, POLR3G, MASS1 | |
| | | | | | 7q33 | Loss | 3,000 | 136,255,000-136,258,000 | No/NS | No known genes | |
| | | | | | 8q23.2 | Loss | 32,000 | 111,182,000-111,214,000 | No/NS | No known genes | |
| | | | | | 9p21.3 | Loss | 8,200 | 25,073,900-25,082,100 | Yes/NS | No known genes | |
| | | | | | 11q25 | Gain | 369,000 | 133,855,000-134,224,000 | No/S | No known genes | |
| | | | | | 12q21.33 | Gain | 19,700 | 90,807,700-90,827,400 | Yes/NS | No known genes | |
| | | | | | 13q21.32 | Loss | 2,500 | 65,576,300-65,578,800 | Yes/NS | No known genes | |

TABLE 1-continued

| Sample ID | Phenotype/Family type | Cytogenetic Analysis Karyotype | Breakpoint Location | RefSeq Genes | CNV Analysis Chr | CNV | Size (bp) | Location | AS/Str[a] | RefSeq Genes | Comments |
|---|---|---|---|---|---|---|---|---|---|---|---|
| 15 SK0043-003 (29346) | Multiplex family ASD | 46, XY, t(6; 9)(q10; q12) unknown | 6q11.2-q12: 63,464,452-63,511,410 9q21.11: 68,599,032-68,682,365 | No known genes PIP5K1B | 8p23.2 15q11.2 | Loss Gain | 35,040 1,713,200 | 3,984,190-4,019,230 18,376,200-20,089,400 | No/NS No/S | CSMD1 LOC28755, POTE15, OR4M2, OR4N4 | SK Sibling also has ASD but a normal 46, XY karyotype |
| 16 SK0181-004 (52191) | Simplex family ASD | 46, XY, t(6; 14)(q13; q21) de novo | 6q12: 69,241,818-69,279,457 14q21.1-q21.2: 40,807,716-44,806,460 | No known genes LRFN5, c14orf155, c14orf28, BTBD5, KIAA0423, PRPF39, FKBP3, AK093422, KIAA1596, FANCM, c14orf106 | 3p14.1-p13 4q28.3 | Loss Loss | 5,346,900 254,000 | 65,286,300-70,633,200 135,282,000-135,536,000 | Yes/S No/NS | 13 genes No known genes | SK |
| 17 SK0083-003 (50800L) | Simplex family ASD, craniosynostosis, developmental verbal dyspraxia, motor delay | 46, XY, del(7)(q31.1q31.32) de novo | 7q31.1: 108,272,363-108,337,904 7q31.31: 119,007,999-119,335,246 | IMMP2L, LRRN3, DOCK4, ZNF277P, IFRD1 ... to ... AS21, CFTR, CTTNBP2, LSM8, ANKRD7 | 1q31.1 2p23.3 4q35.2 6p24.2 7q31.1-q31.31 7q36.2 8q24.21 10p11.23 14q11.2 17q21.31 | Loss Gain Gain Gain Loss Loss Gain Gain Loss Loss | 15,000 26,300 21,314 188,500 11,023,506 26,297 48,000 26,700 219,458 117,521 | 186,702,000-186,717,000 25,138,000-25,164,300 188,232,000-188,253,314 11,479,600-11,668,100 108,200,381-119,223,887 152,027,450-152,053,747 127,951,000-127,999,000 30,893,400-30,920,100 19,272,965-19,492,423 40,897,617-41,015,138 | No/S Yes/NS Yes/S Yes/NS Yes/S Yes/NS Yes/NS Yes/NS No/S No/NS | No known genes No known genes No known genes No known genes >50 genes No known genes No known genes No known genes OR4K1, OR4N2, OR4M1, OR4K5, OR4Q3, OR4K2 PLEKHM1 | Other Canadian Family Described previously in Feuk et al.[3] |
| 18 SK0131-003 (39989) | Simplex family Autistic features, speech-language disorder (developmental verbal dyspraxia), dysmorphic features, mild developmental delay, unable to cough/sneeze/laugh | 46, XX, del(7)(q31.2q32.2) (D7S486-, D7S522-) de novo, WBS inv-2 de novo | 7q31.1: 113,181,975-113,518,235 7q32.2: 128,540,690-128,796,716 | FOXP2, MDFIC, TFEC, TES, CAV2, CAV1 ... to ... IRF5, TNPO3, TSPAN33, SMO, FAM40B, KIAA0828 | 2p22.2 3p21.31 4q31.21 7p14.1 7q31.1-q32.2 | Loss Gain Gain Gain Loss | 67,740 52,599 120,171 147,076 15,486,721 | 37,848,232-37,915,972 147,754,068-147,806,667 145,146,000-145,266,171 38,096,725-38,243,801 113,335,000-128,821,721 | No/NS Yes/NS No/S No/NS Yes/S | No known genes CCR5, CCRL2, CCR2 GYPE AMPH >50 genes | Other Canadian Family Described previously in Feuk et al.[3] |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| | spontaneously | | | | 8q13.3 | Gain | 261,985 | 72,881,221-73,143,206 | Yes/NS | MSC, TRPA1 | |
| | | | | | 10q11.22 | Gain | 455,100 | 47,030,100-47,485,200 | No/NS | ANXA8 | |
| | | | | | 10q26.2 | Gain | 91,077 | 128,501,014-128,592,091 | Yes/S | DOCK1 | |
| | | | | | 13q21.33 | Loss | 44,235 | 69,634,065-69,678,300 | No/NS | No known genes | |
| | | | | | 14q11.2 | Loss | 222,786 | 19,272,965-19,495,751 | No/NS | OR4K1, OR4N2, OR4M1, OR4K5, OR4Q3, OR4K2 | |
| | | | | | 14q11.2 | Gain | 637,249 | 21,462,466-22,099,715 | No/S | No known genes | |
| | | | | | 15q11.2 | Gain | 1,662,280 | 18,427,103-20,089,383 | No/NS | LOC283755, POTE15, OR4M2, OR4N4 | |
| | | | | | 17q12 | Gain | 29,984 | 31,471,515-31,501,499 | No/NS | No known genes | |
| | | | | | 22q11.22 | Gain | 810,876 | 20,772,047-21,582,923 | No/NS | 6 genes | |
| 19 SK0002-003 (50002) | Simplex family ASD, psychosis | 46,XX, inv(7)(p15.3; q22.1) unknown | 7p21.1: 18,284,397-18,302,387 | No known genes | 4q28.3 | Gain | 765,000 | 132,195,000-132,960,000 | No/S | No known genes | Other Non Canadian-Family |
| | | | 7q22.3: 104,360,659-104,549,945 | SPRK2 | 5p15.1-15.2 | Gain | 239,100 | 14,940,400-15,179,500 | No/S | No known genes | |
| | | | | | 15q11.2 | Gain | 1,713,200 | 18,376,200-20,089,400 | Yes/S | LOC283755, POTE15, OR4M2, OR4N4 | |
| 20 SK0211-003 (58892) | Simplex family ASD, mild elevation of lactate | 46,XX, inv(7)q22q34)mat inherited | 7q21.3: 96,943,657-96,985,663 | No known genes | 7q22.1 | Gain | 379,000 | 100,393,000-100,772,000 | No/NS | 10 genes | Other Non Canadian Family |
| | | | 7q34: 140,920,721-140,958,207 | TAS2R4, TAS2R5 | 9p21.1 | Loss | 135,100 | 30,408,400-30,543,500 | No/NS | No known genes | Mother and unaffected twin sister have the same karyotype; 7q34 breakpoint overlaps with a ASD translocation patient |
| 21 SK0040-003 (55449) | Multiplex family ASD, ADHD, severe anxiety attacks, seizures, difficulties with fine and gross motor skills | 46,XY, t(7; 8)(p15; q22), t(10; 11)(q26; q23) unknown | 7p15.3: 21,825,126-21,869,196 | No known genes | 2q37.3 | Loss | 95,959 | 242,634,423-242,730,382 | No/S | No known genes | Other Non-Canadian Family |
| | | | 8q22.2: 99,652,299-99,823,618 | STK3 | 10q21.3 | Loss | 144,903 | 67,734,600-67,879,503 | No/S | CTNNA3 | Unaffected sister with normal female karyotype, has difficulties in |
| | | | | | 11q22.3 | Loss | 62,995 | 104,729,456-104,792,451 | No/NS | No know genes | |

TABLE 1-continued

| Sample ID | Phenotype/Family type | Cytogenetic Analysis Karyotype | Breakpoint Location | RefSeq Genes | CNV Analysis Chr | CNV | Size (bp) | Location | AS/Str[a] | RefSeq Genes | Comments |
|---|---|---|---|---|---|---|---|---|---|---|---|
| | | | 10q26: 127,985,179-131,365,091 | Multiple genes | 14q11.2 | Gain | 219,458 | 19,272,965-19,492,423 | No/NS | OR4K2, OR4N2, OR4K1, OR4K5 | some muscles, difficulties with fine and gross motor skills, severe anxiety attacks, not able to relate to peers and is affected by noise |
| | | | | | 14q11.2 | Gain | 224,329 | 21,784,072-22,008,401 | No/NS | No known genes | |
| | | | 11q23: 109,979,883-111,597,476 | Multiple genes | 15q11.2 | Gain | 1,662,280 | 18,427,103-20,089,383 | No/S | LOC283755, POTE15, OR4M2, OR4N4 | |
| | | | | | 22q11.22 | Loss | 515,645 | 21,031,117-21,546,762 | No/NS | PRAME, SUHW2, SUHW1, GGTL4 | |
| | | | | | 22q11.23 | Gain | 269,129 | 23,975,202-24,244,331 | No/S | CTA, LRP5L | |
| 22 SK0145-003 (67955) | Simplex family ASD | 46, XX, t(7; 11)(q31; q25)mat inherited | 7q31.2: 114,573,150-114,611,613 | No known genes | 1p36.11 | Gain | 192,600 | 26,231,500-26,424,100 | Yes/NS | 8 genes | Other Canadian Family Apparently unaffected mother has the same 7q31.2 and 11q25 breakpoints |
| | | | 11q25: 133,882,647-134,001,155 | No known genes | 2p24.2 | Gain | 14,233 | 17,416,366-17,430,599 | Yes/NS | No known genes | |
| | | | | | 3p23 | Gain | 28,509 | 34,844,620-34,873,129 | Yes/NS | No known genes | |
| | | | | | 5p15.33 | Gain | 3,029,476 | 165,712-3,195,188 | Yes/NS | 28 genes | |
| | | | | | 6p22.2 | Gain | 25,841 | 25,576,804-25,602,645 | Yes/NS | LRRC16 | |
| | | | | | 7p14.1 | Gain | 20,412 | 37,494,999-37,515,411 | No/NS | No known genes | |
| | | | | | 8q13.3 | Gain | 28,933 | 72,911,162-72,940,095 | Yes/NS | MSC | |
| | | | | | 10p12.1 | Loss | 98,961 | 27,642,965-27,741,926 | No/S | PTCHD3 | |
| | | | | | 12p12.3 | Gain | 37,831 | 18,855,833-18,893,664 | Yes/NS | No known genes | |
| | | | | | 14q11.2 | Gain | 464,929 | 21,551,291-22,016,220 | No/NS | No known genes | |
| | | | | | 15q23-24.1 | Gain | 435,603 | 70,053,228-70,488,831 | Yes/NS | 9 genes | |
| | | | | | 19q13.43 | Gain | 308,600 | 63,476,500-63,785,100 | Yes/NS | 18 genes | |
| 23 SK0031-003 (68160L) | Simplex family ASD, very little language, global developmental delays | 46, XY, t(7; 13)(q31.3; q21) mat inherited | 7q31.2: 116,270,156-116,458,896 | ST7 | 5p13.2 | Loss | 3,000 | 36,495,800-36,498,800 | Yes/NS | No known genes | Other Non Canadian Family |
| | | | 13q21.1: 54,559,087-54,739,454 | No known genes | 6p22.1-21.33 | Gain | 79,600 | 29,967,200-30,046,800 | No/NS | HLA-A | |
| | | | | | 9p23 | Loss | 112,800 | 11,895,600-12,008,400 | No/NS | No known genes | |
| | | | | | 14q32.2 | Gain | 772,400 | 99,015,100-99,787,500 | Yes/S | 8 genes | |
| | | | | | 15q11.2 | Gain | 1,378,000 | 18,711,400-20,089,400 | No/S | LOC283755, POTE15, OR4M2, OR4N4 | |

TABLE 1-continued

| Sample ID | Phenotype/Family type | Cytogenetic Analysis Karyotype | Breakpoint Location | RefSeq Genes | CNV Analysis Chr | CNV | Size (bp) | Location | AS/Str[a] | RefSeq Genes | Comments |
|---|---|---|---|---|---|---|---|---|---|---|---|
| | | | | | 17q21.31 | Gain | 597,300 | 41,569,000-42,166,300 | No/NS | 6 genes | |
| | | | | | 22q11.23 | Gain | 251,200 | 23,989,000-24,240,200 | No/S | CTA-246H3.1, LRP5L | SK Described previously in Kwasnicka-Crawford et al.[4] |
| 24 SK0073-003 (57283L) | Simplex family ASD, developmental delay, delayed expressive and receptive language | 47, XX, idic(15)(q13) de novo | 15q13: 28,918,525-31,848,963 | LOC400968, LOC283755, POTE15, OR4M2, OR4N4 ... to ... ARHGAP11A, c15orf45, GREM1, RYR3 | 1q25.2 | Gain | 424,000 | 176,522,000-176,946,000 | Yes/NS | 6 genes | |
| | | | | | 2p23.3 | Gain | 703,500 | 24,701,300-25,404,800 | Yes/NS | 7 genes | |
| | | | | | 4p16.3 | Gain | 997,460 | 1,692,240-2,689,700 | Yes/NS | 12 genes | |
| | | | | | 4q35.1 | Gain | 311,000 | 185,856,000-186,167,000 | Yes/NS | CASP3, CCDC111, MLF1IP, ACSL1 | |
| | | | | | 5q31.1 | Gain | 93,000 | 134,426,000-134,519,000 | Yes/S | No known genes | |
| | | | | | 9p21.1 | Loss | 362,900 | 30,452,800-30,815,700 | Yes/NS | No known genes | |
| | | | | | 14q11.2 | Gain | 414,900 | 21,660,700-22,075,600 | No/NS | No known genes | |
| | | | | | 15q11.2-13.3 | Gain | 11,922,600 | 18,376,200-30,298,800 | Yes/S | >50 genes | |
| | | | | | 16p11.2 | Gain | 1,543,900 | 28,062,200-29,606,100 | No/NS | >20 genes | |
| | | | | | 16p11.2 | Gain | 658,600 | 30,589,900-31,248,500 | No/NS | >20 genes | |
| 25 SK0218-003 (60340) | Multiplex family ASD, cleft palate, club feet, mild-facial hypoplasia, heart defect | 46, XX, del(18)(q21) de novo | 18q21.32: 55,690,398-55,884,029 | See CNV | 12p13.33 | Loss | 92,328 | 1,760,084-1,852,412 | Yes/S | CACNA2D4, ADIPOR2, LRTM2 | SK As noted in the Autism Chromosome Rearrangement Database there are 5 addition reported cases of abnormalities involving 18q; Sibling has a normal 46, XY karyotype also is affected with autism and has oromotor difficulties. |
| | | | | | 15q11.2 | Loss | 1,613,450 | 18,446,422-20,059,872 | No/S | LOC283755, POTE15, OR4M2, OR4N4 | |
| | | | | | 17q21.31 | Gain | 190,234 | 41,518,415-41,708,649 | No/NS | KIAA1267 | |
| | | | | | 18q21.32-q23 | Loss | 20,358,999 | 55,756,601-76,115,600 | Yes/S | >50 genes | |
| | | | | | 19q13.42 | Loss | 68,786 | 59,971,717-60,040,503 | No/NS | KIR3DP1, KIR2DL1, KIR3DL1, KIR2DL4, KIR2DS4 | |
| | | | | | 20p11.23 | Gain | 128,457 | 19,740,012-19,868,469 | Yes/NS | RIN2 | |

TABLE 1-continued

| Sample ID | Phenotype/Family type | Cytogenetic Analysis | | | CNV Analysis | | | | | | |
|---|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| 26 SK0215-006 (58449) | Simplex family ASD | 46, XY, t(19; 21)(p13.2; q22.12) inherited | 19p13.2: 7,804,294-7,896,711 21q22.12: 36,091,999-36,191,098 | EVI5L, FLJ22184, LRRC8E, MAP2K7, SNAPC2, CTXN1 No known genes | 1p21.3 | Loss | 1,092,500 | 97,271,600-98,364,100 | Yes/S | FLJ35409, DPYD | Other Canadian Family Patient has an unaffected sister with the same karyotype |
| 27 SK0136-003 (51253) | Simplex family ASD | 46, X, der(Y)t(Y; 15) (q12; p11.2) pat inherited | Not available | | 17p11.1-p11.2 | Gain | 503,100 | 21,634,900-22,138,000 | Yes/NS | FAM27L | |
| | | | | | 4p13 | Gain | 42,400 | 44,809,500-44,851,900 | No/NS | No known genes | |
| | | | | | 8p23.2 | Gain | 234,580 | 2,335,310-2,569,890 | No/NS | No known genes | |
| | | | | | 8q24.23 | Loss | 138,000 | 137,757,000-137,895,000 | No/NS | No known genes | SK |
| | | | | | 10p12.1 | Loss | 51,400 | 27,690,500-27,741,900 | No/NS | PTCHD3 | |
| | | | | | 15q11.2 | Loss | 558,300 | 18,676,700-19,235,000 | No/NS | LOC283755 | |
| | | | | | 15q26.3 | Gain | 388,100 | 99,827,900-100,216,000 | No/NS | PCSK6, TARSL2, TM2D3, OR4F6 | |
| 28 SK0243-003 (67941) | Simplex Family ASD | 46, XY, del(15)(q23q24.2) de novo | See CNV | See CNV | 1q21.1 | Loss | 333,539 | 145,700,996-146,034,535 | No/NS | No known genes | |
| | | | | | 2p22.2 | Gain | 52,951 | 37,847,789-37,900,740 | No/NS | No known genes | SK |
| | | | | | 3q27.3 | Gain | 91,422 | 187,897,578-187,989,000 | No/S | KNG1, EIF4A2 | |
| | | | | | 7p22.3 | Gain | 29,778 | 141,322-171,100 | No/NS | No known genes | |
| | | | | | 7p14.1 | Loss | 32,636 | 38,092,579-38,125,215 | No/NS | No known genes | |
| | | | | | 10p13 | Loss | 1,570 | 13,096,593-13,098,163 | No/NS | No known genes | |
| | | | | | 11p15.1 | Gain | 21,766 | 18,905,796-18,927,562 | No/NS | MRGPRX1 | |
| | | | | | 15q23-q24.2 | Loss | 4,289,500 | 69,601,300-73,890,800 | Yes/S | 55 genes | |
| | | | | | 17q12 | Gain | 38,247 | 31,463,252-31,501,499 | No/NS | No known genes | |
| | | | | | 17q21.31 | Gain | 83,359 | 41,636,474-41,719,833 | No/NS | No known genes | |
| 29 SK0245-005 (68517) | Simplex Family ASD, epicanthal folds, drooping eyes | 46, XY, trp(15)(q11.2q13) de novo | See CNV | See CNV | 6q14.1 | Loss | 47,288 | 79,036,117-79,083,405 | No/NS | No known genes | |
| | | | | | 7p14.1 | Loss | 57,861 | 38,067,354-38,125,215 | No/NS | No known genes | SK |
| | | | | | 10p13 | Loss | 2,538 | 13,095,625-13,098,163 | No/NS | TARP | |
| | | | | | 11p15.1 | Loss | 12,459 | 18,905,796-18,918,255 | No/NS | MRGPRX1 | |

TABLE 1-continued

| Sample ID | Phenotype/Family type | Cytogenetic Analysis Karyotype | Breakpoint Location | RefSeq Genes | Chr | CNV | Size (bp) | CNV Analysis Location | AS/Str[a] | RefSeq Genes | Comments |
|---|---|---|---|---|---|---|---|---|---|---|---|
| | | | | | 14q11.2 | Loss | 219,458 | 19,272,965-19,492,423 | No/S | 6 genes | |
| | | | | | 14q32.33 | Gain | 27,408 | 106,223,861-106,251,269 | No/NS | No known genes | |
| | | | | | 15q11.2-q13.3 | Gain | 11,871,747 | 18,427,100-30,298,847 | Yes/S | >50 genes | |
| | | | | | 19p13.2 | Loss | 132,251 | 6,902,567-7,034,818 | No/S | EMR4, FLG25758, MBD3L2, ZF557 | |
| 30 NA0097-000 (82361L) | Simplex Family ASD | 46, XX, t(11; 12)(q23.3; p13.3) unknown | 11q23: not available | | 2p25.3-2p15 | Gain | 63,451,406[b] | 2,994-63,454,400 | Yes/S | >50 genes | NFLD |
| | | | | | 3p24.2 | Loss | 159,273 | 25,980,400-26,139,673 | No/NS | No known genes | |
| | | | | | 12p11.21 | Gain | 236,006 | 31,065,545-31,301,551 | No/S | DDX11, OVOS2 | |
| | | | 12p13.32-p13.31: 4,341,718-7,918,138 | Multiple genes | 14q11.2 | Gain | 489,269 | 21,498,204-21,987,473 | No/NS | No known genes | |
| | | | | | Xp22.33-Xp22.31 | Loss | 5,825,311 | 34,419-5,859,730 | Yes/S | 21 genes | |
| 31 SK0300-003 (77447) | Multiplex Family ASD, NF1 | 46, X, inv(Y) (p11.2q11.2)pat inherited | Not available | | 4p16.1 | Gain | 35,832 | 7,801,488-7,837,320 | Yes/NS | SORCS2 | |
| | | | | | 5p15.33 | Gain | 124,630 | 752,190-876,820 | No/S | ZDHHC11 | |
| | | | | | 6p25.1 | Loss | 215,567 | 4,200,904-4,416,471 | Yes/S | No known genes | SK |
| | | | | | 8q24.23 | Loss | 198,193 | 137,757,137-137,955,330 | No/S | No known genes | |
| | | | | | 11p15.4 | Loss | 54,390 | 6,845,440-6,899,830 | Yes/S | OR10A2, OR10A4, OR2D2, OR2D3 | |
| | | | | | 14q11.2 | Loss | 229,676 | 19,272,965-19,502,641 | No/NS | 6 genes | |
| | | | | | 15q11.2 | Loss | 1,908,356 | 18,427,103-20,335,459 | No/S | LOC283755, POTE15, OR4M2, OR4N4 | |
| | | | | | | | | Error! Hyperlink reference not valid. | | | |
| | | | | | 15q21.2 | Gain | 183,903 | 48,583,127-48,767,030 | Yes/S | TRPM7, USP50 | |
| | | | | | Xp11.23 | Loss | 83,750 | 47,643,250-47,727,000 | No/S | ZNF630, SSX6 | |
| 32 SK0094-005 (49304) | Multiplex Family ASD | 46, XX, ins(21; ?)(p11.2; ?) unknown | Not available | | 7q21.2 | Loss | 509,800 | 90,919,200-91,429,000 | Yes/NS | MTERF, AKAP9, CYP51A1, LOC401387 | SK |
| | | | | | 9q32 | Gain | 211,000 | 112,463,000-112,674,000 | No/NS | KIAA1958, C9orf80 | |

TABLE 1-continued

| Sample ID | Phenotype/Family type | Cytogenetic Analysis | | | CNV Analysis | | | | | |
|---|---|---|---|---|---|---|---|---|---|---|
| | | Karyotype | Breakpoint Location | RefSeq Genes | Chr | CNV | Size (bp) | Location | AS/Str[a] | RefSeq Genes | Comments |
| | | | | | 10q11.22 | Gain | 124,800 | 47,030,100-47,154,900 | No/NS | No known genes | |
| | | | | | 14q32.33 | Gain | 186,000 | 105,829,000-106,015,000 | No/NS | No known genes | |
| | | | | | Xq23 | Loss | 888,000 | 112,325,000-113,213,000 | Yes/NS | No known genes | |

Affymetrix GeneChip Human Mapping 500K Array Set

For each sample, approximately 500,000 SNPs were genotyped using the combined two-chip NspI and StyI GeneChip® Human Mapping Commercial or Early Access Arrays (Affymetrix, Inc., Santa Clara, Calif.) according to the manufacturer's instructions and as described previously (Kennedy et al. 2003 *Nat Biotechnol.* 21:1233-7, the contents of which are incorporated herein by reference). Briefly, 250 ng of genomic DNA was digested with NspI and StyI restriction enzyme (New England Biolabs, Boston, Mass.), ligated to an adaptor and amplified by PCR. The PCR products were then fragmented with DNaseI to a size range of 250 bp to 2,000 bp, labelled, and hybridized to the array. After hybridization, arrays were washed on the Affymetrix fluidics stations, stained, and scanned using the Gene Chip Scanner 3000 7G and Gene Chip Operating System. Data has been submitted to the Gene Expression Omnibus database (accession GSE9222). Karyotypes were generated using standard clinical diagnostic protocols.

Characterization of Copy Number Variation

NspI and StyI array scans were analyzed for copy number variation using a combination of DNA Chip Analyzer (dChip) (Li and Wong 2001 *Genome Biology* 2: 0032.1-0032.11), Copy Number Analysis for GeneChip (CNAG) (Nannya 2005 *Cancer Res.* 65:6071-9) and Genotyping Microarray based CNV Analysis (GEMCA) (Komura 2006 *Genome Res.* 16:1575-84). Each of these references is incorporated herein by reference.

Analysis with dChip (www.dchip.org) was performed as previously described (Zhao et al 2005 *Cancer Res.* 65:5561-70) in batches of ~100 probands. Briefly, array scans were normalized at the probe intensity level with an invariant set normalization method. After normalization, a signal value was calculated for each SNP using a model-based (PM/MM) method. In this approach, image artifacts were identified and eliminated by an outlier detection algorithm. For both sets of arrays, the resulting signal values were averaged across all samples for each SNP to obtain the mean signal of a diploid genome. From the raw copy numbers, the inferred copy number at each SNP was estimated using a Hidden Markov Model (HMM).

For analyses with CNAG version 2.0 (www.genome.umin.jp), the reference pool was set to include all samples and performed an automatic batch pair-wise analysis using sex-matched controls. Test samples were compared to all samples within the reference pool and matched based on signal intensity standard deviations. The scan intensities for each 'test' sample were compared to the average intensities of the reference samples (typically the average of 5-12 samples) and used to calculate raw copy number changes. Underlying copy number changes were then inferred using a Hidden Markov Model (HMM) built into CNAG.

GEMCA analysis was performed essentially as described (Komura et al. Genome Res 2006; 16(12):1575-84) with the exception that two designated DNA samples (NA10851 and NA15510) were used as references for pair-wise comparison to all proband experiments. These results were further filtered by only including those CNVs that were common to both pair-wise experiments.

CNVs were merged if they were detected in the same individual by more than one algorithm using the outside probe boundaries.

Controls and Autism Chromosome Rearrangement Database (ACRD)

Control samples consisted of (i) CNVs observed in 500 Europeans from the from the German PopGen project (Krawczak et al. Community Genet 2006; 9(1):55-61), and CNVs found in a cohort of 1000 Caucasian non-disease controls from the Ontario population (ref. 24). The ACRD that had 834 putative CNVs or breakpoints mapped to the genome was established. A CNV was considered ASD-specific if it was >10 kb, contained at least three probes and at least 20% of its total length was unique when compared to controls.

CNV Validation Experiments and Balance Rearrangement Breakpoint Mapping

PCR validation of CNV calls was performed using Quantitative Multiplex PCR of short fluorescent fragments (QMPSF) (Redon et al. *Nature.* 444:444-54) or SYBR-Green 1 based real-time quantitative PCR (qPCR) using controls at the ACCN1, CFTR or FOXP2 loci (PMID: 14552656). For both methods, primers were designed using the program PRIMER3 (http://frodo.wi.mit.edu/). Balanced rearrangements were mapped primarily using FISH (Nannya et al. Cancer Res 2005; 65(14):6071-9). The microdel program (Komura et al., ibid) was used to score CNV losses.

For QMPSF, short genomic sequences (140-220 bp) within putative CNVs were PCR amplified using dye-labelled primers corresponding to unique sequences. Each reaction also included co-amplified control amplicons corresponding to either ACCN1 or CFTR located at 17q11.2 and 7q31.2, respectively. Briefly, 40 ng of genomic DNA was amplified by PCR in a final volume of 25 µl using AmpliTaq® DNA polymerase (manufactured for Applied Biosystems by Roche Molecular Systems, Inc.) After an initial step of denaturation at 95° C. for 5 minutes conditions were as follows: 25 PCR cycles of 94° C. for 30 seconds, annealing at 60° C. for 45 seconds, and extension at 72° C. for 30 seconds. A final extension step at 72° C. for 15 minutes followed. QMPSF amplicons were separated on an ABI 3730xl DNA Analyzer (Applied Biosystems, Foster City, Calif.), and analyzed using ABI GeneMapper® software version 3.7 (Applied Biosystems). After adjustment of control amplicons to the same heights, the QMPSF pattern generated from test DNA was superimposed to that of the control DNA. For each putative CNV locus, the copy number ratio was determined by dividing the normalized peak height obtained from the test DNA by that of the control DNA. Peak ratios of >1.4 and <0.7 were indicative of copy number gains and losses, respectively. At least two independent QMPSF assays were required for CNV confirmation.

SYBR Green 1-based real-time qPCR amplification was performed using a Mx3005P quantitative PCR system (Stratagene, La Jolla, USA). Non-fluorescent primers were designed to amplify short genomic fragments (<140 bp) in putative CNV loci. Each assay also included amplification of a control amplicon corresponding to FOXP2 at 7q31.1 for comparison. After optimization of primer sets with control genomic DNA using 'Brilliant® SYBR® Green QPCR Master Mix' (Stratagene), test samples were assayed in 15 µl reaction mixtures in 96-well plates containing: 7.5 µl of reaction mix, 1.8 µl of primer, 6.0 ng of genomic DNA at 1.2 ng/µl, 0.225 µl of reference dye with 1:500 dilution, and 0.475 µl of water. PCR conditions consisted of 10 minutes of polymerase activation at 95° C., followed by 40 cycles of: 95° C. for 15 seconds and a single step at 60° C. for 1 minute for annealing and elongation. These steps were then followed by a final cycle of 95° C. for 1 minute, 55° C. for 30 seconds, and 95° C. for 30 seconds. Standard curve quantification was analyzed by MxPro-Mx3005P software (version 3.20 Build 340) to calculate copy number changes. Coefficient of variation (CV) was calculated on all sample Ct values to remove possible outlier when CV was greater than 1%. The average quantity of the putative CNV locus was divided by the average quantity of the control amplicon on FOXP2. Ratios of >1.4 and <0.7 were indicative of copy number gains and losses, respectively. Each putative CNV locus had at least two independent assays.

Results

Structural Variation Characteristics in ASD Cases

A total of 426 ASD index cases were tested for CNV content including 394 typical idiopathic cases and 32 others that were enrolled based on prior knowledge of having a cytogenetic abnormality. The Affymetrix 500 k SNP array was used because it provided the highest resolution screen available for both SNP genotype and CNV data. Using the SNPs, the ancestry of each sample was categorized (to guide selection of controls). Backgrounds of the samples were found to be: 90.3%, 4.5%, 4.5%, and 0.7%, European, European/mixed, Asian, or Yoruban, respectively.

To maximize CNV discovery, three calling algorithms were used as described above (see FIG. 1) and common results between them were merged to identify a 'full' dataset of 3389 independent CNVs (~8 CNVs per genome, mean size 390 kb) (see Table 4 below). To minimize potential false positives, a second dataset was generated whereby a CNV needed to be detected by two or more algorithms and/or on both the NspI or StyI microarrays (Pinto et al. Hum Mol Genet 2007; 16 Spec No 2:R168-73).

This 'stringent' dataset contained 1312 CNVs (~3 CNVs per genome, mean size 603 kb). Using q-PCR, 48% (12/26) and 96% (48/50) of random CNVs were validated in the full and stringent collections, respectively.

TABLE 4

Summary of CNV in ASD and Controls

| | POPGEN CONTROLS | | AUTISM PROBANDS | | | |
| --- | --- | --- | --- | --- | --- | --- |
| | All CNVs | | All CNVs | | Autism Specific[1] | |
| | Full | Stringent[2] | Full | Stringent[2] | Full | Stringent[2] |
| #samples | 500 | 500 | 426 | 426 | 426 | 426 |
| #CNVs | 3695 | 1558 | 3389 | 1312 | 888 | 276 |
| CNV/Genome[3] | 7.4 | 3.1 | 8.0 | 3.1 | 2.1 | 0.65 |
| Mean/Median Size (kb) | 315/151 | 470/224 | 390/162 | 603/219 | 518/121 | 1082/194 |
| % Gain/Loss | 59/41% | 70/30% | 58/42% | 62/38% | 61/39% | 57/43% |
| Overlapping CNV/Loci (%)[4] | 3005/333 (81%) | 1226/142 (78%) | 2728/277 (80%) | 980/94 (74%) | 397/122 (44%) | 30/13 (11%) |
| >1 Mb CNV (%) | 343 (9%) | 250 (16%) | 339 (10%) | 212 (16%) | 63 (7%) | 32 (12%) |

[1] Not seen in controls.
[2] Stringent dataset as called by >1 algorithms or arrays. Analysis with dChip was performed in batches of ~100 probands. For CNAG version 2.0, the reference pool was set to include all samples and performed an automatic batch pairwise analysis using sex-matched controls. For GEMCA two designated DNA samples (NA10851 and NA15510) were used as references for pairwise comparison to all proband experiments. These results were further filtered by only including those CNVs that were common to both pairwise experiments. In all instances CNVs were merged if they were detected in the same individual by more than one algorithm using the outside probe boundaries.
[3] CNV/genome breakdown by algorithm: dChip Merged (3.0/genome), CNAG Merged (5.6/genome), GEMCA (5.5/genome). Validation experiments using q-PCR and FISH are described in the text. Another form of validation comes from examining the trios where we can demonstrate inheritance in 48 (maternal is 25, paternal is 23) of the autism-specific stringent dataset. Also from the trios, 148 confirmed regions (inheritance assignment) in the stringent dataset that overlap with controls (maternal is 65, paternal is 83).
[4] Represents the total number of overlapping and/or recurrent CNVs, the number of overlapping/CNV loci, and the percentage of overlapping CNVs, out of the total dataset.

Five hundred European control samples were examined for their CNV content and similar numbers of CNVs (3695 in the full and 1558 in the stringent dataset) were found to those in the ASD cases (Table 4). This suggested germ-line chromosome instability was not a significant contributing mechanism. The ASD CNVs were then compared against the 500 European/Caucasian controls and the *Database of Genomic Variants* (a repository of structural variation in 'non-disease' populations) (Iafrate et al. Nat Genet 2004; 36(9):949-51) to establish autism-specific CNV datasets. The subsequent analysis then focused on the 276 CNVs in the stringent autism-specific category, which mapped across all 23 chromosomes (FIG. 2), details of which are found in Table 3, below. Additional ASD-relevant CNV data is also found in the other categories in Table 5 (discussed below).

TABLE 3

| FAM ID (DNA) | Sex | Type | Chr | start | stop | size | CNV | CNV Category |
| --- | --- | --- | --- | --- | --- | --- | --- | --- |
| SK0215-006 (58449) | M | CHR | 1 | 97,271,600 | 98,364,100 | 1,092,500 | loss | CNVs confirmed de novo |
| SK0152-003 (41548L) | M | CHR | 3 | 15,125,800 | 16,535,400 | 1,409,600 | loss | CNVs confirmed de novo |
| SK0181-003 (52191) | M | CHR | 3 | 65,286,300 | 70,633,200 | 5,346,900 | loss | CNVs confirmed de novo |
| SK0205-004 (56242) | F | CHR | 5 | 81,949 | 13,882,933 | 13,800,984 | loss | CNVs confirmed de novo |
| SK0152-003 (41548L) | M | CHR | 5 | 9,275,811 | 12,705,200 | 3,429,389 | loss | CNVs confirmed de novo |
| SK0083-003 (50800L) | M | CHR | 7 | 108,200,381 | 119,223,887 | 11,023,507 | loss | CNVs confirmed de novo |
| SK0131-003 (39989) | F | CHR | 7 | 113,335,000 | 128,821,721 | 15,486,722 | loss | CNVs confirmed de novo |
| SK0262-003 (68609) | M | SPX | 8 | 710,491 | 1,501,580 | 791,089 | gain | CNVs confirmed de novo |

TABLE 3-continued

| FAM ID (DNA) | Sex | Type | Chr | start | stop | size | CNV | CNV Category |
|---|---|---|---|---|---|---|---|---|
| SK0152-003 (41548L) | M | CHR | 12 | 40,584,198 | 41,007,040 | 422,842 | loss | CNVs confirmed de novo |
| MM0278-003 (57788) | M | SPX | 12 | 114,170,000 | 132,388,000 | 18,218,001 | gain | CNVs confirmed de novo |
| SK0243-003 (67941) | M | CHR | 15 | 69,601,300 | 73,890,800 | 4,289,500 | loss | CNVs confirmed de novo |
| NA0067-000 (65344L) | M | SPX | 16 | 87,800,593 | 88,066,260 | 265,668 | loss | CNVs confirmed de novo |
| SK0218-003 (60340) | F | CHR | 18 | 55,756,601 | 76,115,600 | 20,358,999 | loss | CNVs confirmed de novo |
| MM0109-003 (46486) | F | SPX | 20 | 60,949,339 | 62,377,000 | 1,427,662 | gain | CNVs confirmed de novo |
| SK0244-003 (69183) | M | SPX | 21 | 42,974,148 | 43,328,084 | 353,936 | loss | CNVs confirmed de novo |
| NA0039-000 (69736) | F | CHR | 22 | 46,277,400 | 49,509,100 | 3,231,700 | loss | CNVs confirmed de novo |
| MM0109-003 (46486) | F | SPX | 22 | 49,243,247 | 49,519,949 | 276,703 | loss | CNVs confirmed de novo |
| NA0097-000 (82361L) | F | CHR | X | 34,419 | 5,859,730 | 5,825,312 | loss | CNVs confirmed de novo |
| SK0306-004 (78681) | F | SPX | X | 48,073,600 | 52,716,966 | 4,643,367 | gain | CNVs confirmed de novo |
| SK0147-003 (47544L) | F | SPX | 2 | 114,855,796 | 115,334,166 | 478,371 | loss | CNVs Recurrent/Overlapping |
| SK0167-003 (60966L) | F | MPX | 2 | 114,855,796 | 115,334,166 | 478,371 | gain | CNVs Recurrent/Overlapping |
| SK0288-003 (75420) | F | SPX-MZ | 2 | 115,141,880 | 115,247,000 | 105,121 | gain | CNVs Recurrent/Overlapping |
| NA0030-000 (55240) | M | SPX | 2 | 186,674,000 | 186,786,323 | 112,324 | loss | CNVs Recurrent/Overlapping |
| SK0306-004 (78681) | F | SPX | 2 | 186,674,000 | 186,771,130 | 97,131 | loss | CNVs Recurrent/Overlapping |
| MM0220-003 (61180L) | M | MPX | 6 | 118,799,000 | 119,117,000 | 318,001 | gain | CNVs Recurrent/Overlapping |
| NA0025-000 (60490) | M | SPX | 6 | 118,823,011 | 119,117,000 | 293,990 | gain | CNVs Recurrent/Overlapping |
| SK0190-003 (54742) | M | SPX | 7 | 152,698,000 | 154,478,000 | 1,780,000 | gain | CNVs Recurrent/Overlapping |
| SK0115-003 (40555) | M | SPX | 7 | 153,098,000 | 153,372,000 | 274,001 | gain | CNVs Recurrent/Overlapping |
| SK0058-003 (59963) | M | MPX | 7 | 153,539,745 | 153,556,533 | 16,789 | gain | CNVs Recurrent/Overlapping |
| SK0143-003 (36812) | M | SPX | 8 | 53,481,200 | 53,766,400 | 285,201 | gain | CNVs Recurrent/Overlapping |
| MM0236-004 (46475) | M | MPX | 8 | 53,724,445 | 53,996,124 | 271,680 | gain | CNVs Recurrent/Overlapping |
| SK0270-003 (71341) | M | SPX | 9 | 7,725,280 | 7,764,180 | 38,900 | loss | CNVs Recurrent/Overlapping |
| MM0103-003 (42387) | M | MPX | 9 | 7,725,283 | 7,760,233 | 34,951 | loss | CNVs Recurrent/Overlapping |
| MM0272-003 (45563) | M | MPX | 11 | 40,285,800 | 40,548,738 | 262,939 | loss | CNVs Recurrent/Overlapping |
| SK0167-003 (60966L) | F | MPX | 11 | 40,417,554 | 40,610,400 | 192,847 | loss | CNVs Recurrent/Overlapping |
| SK0023-003 (58096) | M | SPX | 13 | 66,470,851 | 66,660,289 | 189,438 | gain | CNVs Recurrent/Overlapping |
| MM0299-003 (51674) | F | MPX | 13 | 66,487,899 | 66,660,300 | 172,402 | gain | CNVs Recurrent/Overlapping |
| MM0109-003 (46486) | F | SPX | 16 | 21,441,805 | 22,688,093 | 1,246,289 | gain | CNVs Recurrent/Overlapping |
| MM0289-003 (42267) | F | MPX | 16 | 21,808,800 | 22,611,363 | 802,556 | loss | CNVs Recurrent/Overlapping |
| MM0088-003 (45562) | F | MPX | 16 | 29,559,989 | 30,235,818 | 675,830 | loss | CNVs Recurrent/Overlapping |
| NA0133-000 (78119L) | F | SPX | 16 | 29,559,989 | 30,085,308 | 525,320 | gain | CNVs Recurrent/Overlapping |
| SK0091-004 (46407) | F | MPX | 22 | 17,265,500 | 21,546,762 | 4,281,262 | gain | CNVs Recurrent/Overlapping |
| SK0323-003 (80022) | M | MPX | 22 | 18,683,900 | 19,427,000 | 743,101 | gain | CNVs Recurrent/Overlapping |
| SK0123-004 (60536L) | M | MPX | 22 | 47,717,300 | 48,318,828 | 601,528 | gain | CNVs Recurrent/Overlapping |
| MM0102-003 (47598) | M | MPX | 22 | 48,152,289 | 48,232,669 | 80,380 | loss | CNVs Recurrent/Overlapping |
| NA0002-000 (52026) | M | SPX | 7 | 153,585,000 | 153,651,462 | 66,463 | loss | CNVs Recurrent/Overlapping/ CNVs confirmed de novo |
| SK0073-003 (57283L) | F | CHR | 15 | 18,376,200 | 30,298,800 | 11,922,600 | gain | CNVs Recurrent/Overlapping/ CNVs confirmed de novo |
| SK0245-005 (68517) | M | CHR | 15 | 18,427,100 | 30,298,847 | 11,871,747 | gain | CNVs Recurrent/Overlapping/ CNVs confirmed de novo |
| SK0119-003 (35190) | M | MPX | 22 | 17,014,900 | 19,786,200 | 2,771,300 | loss | CNVs Recurrent/Overlapping/ CNVs confirmed de novo |
| SK0297-003 (76066) | M | SPX-MZ | 22 | 17,265,500 | 21,546,762 | 4,281,263 | gain | CNVs Recurrent/Overlapping/ CNVs confirmed de novo |
| MM0109-003 (46486) | F | SPX | 17 | 40,555,289 | 41,089,766 | 534,478 | loss | CNVs that are Singletons |
| MM0240-003 (43743) | F | MPX | 17 | 40,555,289 | 41,128,323 | 573,035 | loss | CNVs that are Singletons |
| NA0074-000 (63358) | M | SPX | 1 | 41,463,611 | 41,924,314 | 460,704 | gain | CNVs that are Singletons |
| SK0036-003 (29186) | F | SPX | 1 | 57,936,233 | 58,514,629 | 578,396 | gain | CNVs that are Singletons |
| MM0236-004 (46475) | M | MPX | 1 | 60,369,204 | 61,426,300 | 1,057,101 | gain | CNVs that are Singletons |
| MM0020-004 (47838) | M | MPX | 1 | 65,649,086 | 65,713,423 | 64,338 | gain | CNVs that are Singletons |
| NA0076-000 (63624) | M | SPX | 1 | 91,930,266 | 92,330,344 | 400,078 | gain | CNVs that are Singletons |
| SK0174-003 (64379L) | M | SPX | 1 | 108,046,000 | 108,246,283 | 200,284 | loss | CNVs that are Singletons |
| SK0283-003 (72309) | F | CHR | 1 | 148,095,537 | 149,547,463 | 1,451,926 | gain | CNVs that are Singletons |
| MM0011-003 (60566L) | M | MPX | 1 | 165,908,677 | 166,028,402 | 119,726 | loss | CNVs that are Singletons |
| SK0132-003 (30661) | M | MPX | 1 | 186,673,899 | 186,716,570 | 42,672 | loss | CNVs that are Singletons |
| NA0109-000 (72873) | M | SPX | 1 | 212,037,558 | 212,471,000 | 433,443 | loss | CNVs that are Singletons |
| SK0183-004 (52217) | M | SPX | 1 | 238,633,145 | 239,606,926 | 973,781 | loss | CNVs that are Singletons |
| MM0219-003 (46823) | M | MPX | 2 | 34,155,700 | 34,253,221 | 97,522 | loss | CNVs that are Singletons |
| MM0295-003 (46488) | M | MPX | 2 | 34,662,196 | 34,780,515 | 118,320 | loss | CNVs that are Singletons |
| NA0083-000 (66104L) | M | SPX | 2 | 34,858,330 | 34,937,455 | 79,125 | loss | CNVs that are Singletons |
| SK0270-003 (71341) | M | SPX | 2 | 39,992,374 | 40,053,300 | 60,926 | loss | CNVs that are Singletons |
| NA0055-000 (59448) | M | SPX | 2 | 41,958,200 | 42,088,448 | 130,249 | loss | CNVs that are Singletons |
| SK0301-003 (77203) | M | MPX | 2 | 52,856,046 | 52,969,575 | 113,530 | loss | CNVs that are Singletons |
| NA0027-000 (60421L) | M | MPX | 2 | 121,623,000 | 121,684,915 | 61,915 | loss | CNVs that are Singletons |
| NA0057-000 (59537) | M | SPX | 2 | 125,496,832 | 125,890,571 | 393,740 | loss | CNVs that are Singletons |
| MM0176-003 (62118L) | M | MPX | 2 | 135,358,000 | 135,471,071 | 113,071 | loss | CNVs that are Singletons |
| SK0225-003 (60921) | M | SPX | 2 | 155,849,451 | 155,988,560 | 139,109 | loss | CNVs that are Singletons |
| SK0192-003 (54877) | M | SPX | 2 | 181,771,621 | 181,944,065 | 172,445 | loss | CNVs that are Singletons |
| NA0007-000 (50611) | M | SPX | 2 | 195,170,000 | 195,217,247 | 47,248 | gain | CNVs that are Singletons |
| SK0283-003 (72309) | F | CHR | 3 | 5,365,500 | 5,409,964 | 44,458 | loss | CNVs that are Singletons |
| MM0210-004 (47376) | M | MPX | 3 | 7,957,390 | 8,250,541 | 293,151 | gain | CNVs that are Singletons |
| NA0044-000 (57097) | M | SPX | 3 | 35,613,300 | 35,928,200 | 314,901 | gain | CNVs that are Singletons |
| SK0021-008 (51504) | M | MPX | 3 | 36,110,965 | 36,215,909 | 104,945 | loss | CNVs that are Singletons |
| MM0154-003 (56678L) | F | MPX | 3 | 50,089,500 | 50,199,200 | 109,701 | gain | CNVs that are Singletons |
| SK0152-003 (41548L) | M | CHR | 3 | 78,902,000 | 78,957,000 | 55,000 | gain | CNVs that are Singletons |

TABLE 3-continued

| FAM ID (DNA) | Sex | Type | Chr | start | stop | size | CNV | CNV Category |
|---|---|---|---|---|---|---|---|---|
| NA0044-000 (57097) | M | SPX | 3 | 82,866,400 | 84,544,763 | 1,678,364 | gain | CNVs that are Singletons |
| SK0023-003 (58096) | M | SPX | 3 | 99,400,957 | 99,484,400 | 83,443 | gain | CNVs that are Singletons |
| NA0018-000 (72622) | M | SPX | 3 | 117,838,700 | 117,937,000 | 98,301 | gain | CNVs that are Singletons |
| NA0003-000 (48474) | M | SPX | 3 | 124,386,373 | 124,456,000 | 69,628 | gain | CNVs that are Singletons |
| NA0090-000 (65410) | M | SPX | 3 | 183,837,706 | 183,940,069 | 102,364 | gain | CNVs that are Singletons |
| NA0044-000 (57097) | M | SPX | 4 | 55,718,164 | 55,811,710 | 93,547 | loss | CNVs that are Singletons |
| NA0016-000 (51524L) | F | SPX | 4 | 114,333,509 | 114,416,051 | 82,542 | gain | CNVs that are Singletons |
| SK0012-003 (58468L) | M | SPX | 4 | 152,993,000 | 153,381,007 | 388,008 | gain | CNVs that are Singletons |
| SK0103-005 (42258) | M | SPX | 4 | 157,615,000 | 157,683,000 | 68,000 | gain | CNVs that are Singletons |
| NA0037-000 (69812) | M | SPX | 4 | 179,692,000 | 179,865,680 | 173,680 | gain | CNVs that are Singletons |
| MM0299-003 (51674) | F | MPX | 4 | 181,968,784 | 182,095,665 | 126,882 | loss | CNVs that are Singletons |
| SK0266-003 (68257) | M | SPX | 4 | 183,466,000 | 183,517,000 | 51,000 | loss | CNVs that are Singletons |
| SK0002-003 (50002) | F | CHR | 5 | 14,940,400 | 15,179,500 | 239,100 | gain | CNVs that are Singletons |
| NA0078-000 (63727) | M | MPX | 5 | 25,125,371 | 25,450,672 | 325,302 | gain | CNVs that are Singletons |
| NA0076-000 (63624) | M | SPX | 5 | 37,409,881 | 37,778,834 | 368,953 | gain | CNVs that are Singletons |
| SK0335-003 (72815) | F | CHR | 5 | 38,534,384 | 38,807,002 | 272,619 | loss | CNVs that are Singletons |
| MM0143-004 (47386) | M | MPX | 5 | 110,440,484 | 110,471,180 | 30,697 | gain | CNVs that are Singletons |
| NA0023-000 (60504L) | F | SPX | 5 | 113,104,916 | 113,178,000 | 73,084 | loss | CNVs that are Singletons |
| SK0118-003 (52027) | M | SPX | 5 | 122,834,399 | 123,029,036 | 194,638 | loss | CNVs that are Singletons |
| SK0077-003 (48226) | M | SPX | 5 | 128,968,799 | 129,433,000 | 464,201 | gain | CNVs that are Singletons |
| SK0300-003 (77447) | M | CHR | 6 | 4,200,904 | 4,416,471 | 215,568 | loss | CNVs that are Singletons |
| MM0212-004 (62223L) | F | MPX | 6 | 17,505,095 | 17,703,208 | 198,114 | gain | CNVs that are Singletons |
| MM0300-003 (47836) | F | MPX | 6 | 27,827,354 | 28,119,631 | 292,278 | gain | CNVs that are Singletons |
| MM0225-004 (60826) | M | MPX | 6 | 69,929,900 | 70,278,043 | 348,144 | gain | CNVs that are Singletons |
| SK0217-003 (59279) | M | SPX | 6 | 112,679,982 | 112,776,094 | 96,112 | gain | CNVs that are Singletons |
| SK0326-003 (81155) | M | SPX | 6 | 137,930,847 | 138,011,644 | 80,798 | gain | CNVs that are Singletons |
| MM0088-003 (45562) | F | MPX | 7 | 2,922,139 | 2,964,895 | 42,757 | loss | CNVs that are Singletons |
| NA0147-000 (77123L) | M | SPX | 7 | 3,946,854 | 4,002,686 | 55,833 | loss | CNVs that are Singletons |
| SK0049-004 (59987L) | M | MPX | 7 | 11,526,500 | 11,560,300 | 33,800 | gain | CNVs that are Singletons |
| SK0132-003 (30661) | M | MPX | 7 | 20,242,925 | 20,345,800 | 102,876 | gain | CNVs that are Singletons |
| NA0145-000 (82058L) | M | SPX | 7 | 47,742,927 | 48,775,200 | 1,032,274 | loss | CNVs that are Singletons |
| SK0119-003 (35190) | M | MPX | 8 | 17,706,313 | 17,738,524 | 32,211 | loss | CNVs that are Singletons |
| SK0262-003 (68609) | M | SPX | 8 | 18,623,000 | 19,442,500 | 819,500 | gain | CNVs that are Singletons |
| SK0077-003 (48226) | M | SPX | 8 | 42,971,601 | 43,820,300 | 848,699 | gain | CNVs that are Singletons |
| SK0294-003 (76222) | M | SPX | 8 | 73,762,894 | 73,798,241 | 35,348 | gain | CNVs that are Singletons |
| SK0076-003 (38712) | F | SPX | 8 | 83,989,256 | 84,141,278 | 152,022 | gain | CNVs that are Singletons |
| MM0241-004 (45547) | M | MPX | 8 | 87,230,811 | 87,498,988 | 268,178 | gain | CNVs that are Singletons |
| MM0210-004 (47376) | M | MPX | 8 | 104,166,572 | 104,947,190 | 780,618 | gain | CNVs that are Singletons |
| SK0194-003 (55078) | M | SPX | 8 | 123,539,127 | 123,644,422 | 105,296 | loss | CNVs that are Singletons |
| SK0292-003 (75896) | F | MPX | 8 | 130,467,000 | 130,529,193 | 62,194 | loss | CNVs that are Singletons |
| MM0007-003 (59978) | M | MPX | 9 | 5,099,530 | 5,235,490 | 135,961 | gain | CNVs that are Singletons |
| MM0711-003 (63583L) | M | MPX | 9 | 16,092,066 | 16,379,100 | 287,035 | gain | CNVs that are Singletons |
| SK0015-003 (49932) | M | MPX | 9 | 19,284,100 | 19,511,500 | 227,400 | gain | CNVs that are Singletons |
| SK0015-003 (49932) | M | MPX | 9 | 19,702,200 | 24,674,100 | 4,971,900 | loss | CNVs that are Singletons |
| SK0278-003 (74431) | M | SPX | 9 | 22,626,541 | 22,747,714 | 121,174 | loss | CNVs that are Singletons |
| SK0148-005 (41350) | F | SPX | 9 | 24,607,036 | 24,682,114 | 75,078 | loss | CNVs that are Singletons |
| MM0020-004 (47838) | M | MPX | 9 | 25,439,100 | 25,535,000 | 95,901 | loss | CNVs that are Singletons |
| NA0105-000 (72085) | M | SPX | 9 | 33,054,336 | 33,294,800 | 240,465 | gain | CNVs that are Singletons |
| NA0147-000 (77123L) | M | SPX | 9 | 84,957,060 | 85,054,672 | 97,613 | loss | CNVs that are Singletons |
| SK0045-003 (58937) | M | MPX | 9 | 109,446,000 | 109,837,000 | 391,000 | gain | CNVs that are Singletons |
| MM0117-003 (59983) | M | MPX | 10 | 2,313,505 | 2,407,102 | 93,598 | loss | CNVs that are Singletons |
| MM0225-004 (60826) | M | MPX | 10 | 4,976,040 | 5,124,511 | 148,472 | gain | CNVs that are Singletons |
| MM1086-004 (76285) | M | MPX | 10 | 31,256,118 | 31,604,509 | 348,392 | loss | CNVs that are Singletons |
| MM0068-003 (60836) | M | MPX | 10 | 68,139,200 | 68,246,027 | 106,828 | loss | CNVs that are Singletons |
| NA0037-000 (69812) | M | SPX | 10 | 104,641,000 | 104,786,777 | 145,778 | loss | CNVs that are Singletons |
| SK0300-003 (77447) | M | CHR | 11 | 6,845,440 | 6,899,830 | 54,391 | loss | CNVs that are Singletons |
| SK0322-003 (79950) | M | SPX | 11 | 33,159,190 | 33,462,070 | 302,881 | gain | CNVs that are Singletons |
| MM0305-003 (47607) | M | MPX | 11 | 68,053,777 | 68,204,900 | 151,123 | gain | CNVs that are Singletons |
| NA0032-000 (55186) | M | SPX | 11 | 76,114,600 | 76,140,500 | 25,900 | gain | CNVs that are Singletons |
| MM0212-004 (62223L) | F | MPX | 11 | 99,148,202 | 99,289,243 | 141,042 | loss | CNVs that are Singletons |
| SK0167-003 (60966L) | F | MPX | 11 | 101,131,785 | 101,246,901 | 115,117 | loss | CNVs that are Singletons |
| MM0112-005 (46736) | M | MPX | 11 | 116,789,980 | 116,855,347 | 65,368 | gain | CNVs that are Singletons |
| MM0240-003 (43743) | F | MPX | 11 | 117,452,000 | 117,539,000 | 87,001 | gain | CNVs that are Singletons |
| SK0255-003 (68785) | M | SPX | 11 | 124,303,460 | 124,719,976 | 416,517 | gain | CNVs that are Singletons |
| NA0065-003 (62798L) | M | SPX | 11 | 125,639,908 | 126,102,027 | 462,120 | gain | CNVs that are Singletons |
| NA0172-000 (80993L) | M | SPX | 12 | 3,727,911 | 3,879,230 | 151,320 | loss | CNVs that are Singletons |
| SK0059-003 (29224) | M | SPX | 12 | 10,431,082 | 10,445,300 | 14,218 | gain | CNVs that are Singletons |
| SK0326-003 (81155) | M | SPX | 12 | 46,170,200 | 46,365,774 | 195,575 | gain | CNVs that are Singletons |
| SK0110-003 (24626) | M | SPX | 12 | 50,520,400 | 50,573,516 | 53,116 | gain | CNVs that are Singletons |
| NA0071-000 (64719L) | F | SPX | 12 | 57,408,270 | 58,532,356 | 1,124,087 | gain | CNVs that are Singletons |
| SK0305-003 (78621) | F | SPX | 12 | 77,239,265 | 77,364,400 | 125,136 | loss | CNVs that are Singletons |
| SK0301-003 (77203) | M | MPX | 12 | 83,388,935 | 83,428,800 | 39,866 | gain | CNVs that are Singletons |
| NA0093-000 (66999) | M | SPX | 12 | 96,496,784 | 96,568,500 | 71,716 | loss | CNVs that are Singletons |
| MM0711-003 (63583L) | M | MPX | 12 | 96,576,486 | 96,639,686 | 63,201 | loss | CNVs that are Singletons |
| SK0292-003 (75896) | F | MPX | 12 | 101,568,000 | 101,586,000 | 18,001 | gain | CNVs that are Singletons |
| NA0109-000 (72873) | M | SPX | 12 | 110,646,607 | 110,800,000 | 153,394 | gain | CNVs that are Singletons |
| MM0210-004 (47376) | M | MPX | 12 | 125,446,000 | 125,757,000 | 311,000 | gain | CNVs that are Singletons |
| SK0079-003 (48388) | M | MPX | 13 | 17,960,300 | 18,492,994 | 532,694 | gain | CNVs that are Singletons |

TABLE 3-continued

| FAM ID (DNA) | Sex | Type | Chr | start | stop | size | CNV | CNV Category |
|---|---|---|---|---|---|---|---|---|
| NA0028-000 (58891L) | M | SPX | 13 | 62,915,912 | 62,977,748 | 61,837 | loss | CNVs that are Singletons |
| SK0326-003 (81155) | M | SPX | 13 | 89,726,966 | 90,134,219 | 407,254 | gain | CNVs that are Singletons |
| NA0048-000 (58569) | M | SPX | 13 | 93,288,520 | 93,344,600 | 56,081 | gain | CNVs that are Singletons |
| SK0326-003 (81155) | M | SPX | 13 | 93,497,400 | 93,732,931 | 235,532 | gain | CNVs that are Singletons |
| SK0254-003 (68687) | M | SPX | 13 | 105,172,000 | 105,357,000 | 185,000 | gain | CNVs that are Singletons |
| SK0121-003 (41288) | M | SPX | 14 | 76,007,842 | 76,924,400 | 916,558 | gain | CNVs that are Singletons |
| SK0031-003 (68160L) | M | CHR | 14 | 99,015,100 | 99,787,500 | 772,400 | gain | CNVs that are Singletons |
| SK0300-003 (77447) | M | CHR | 15 | 48,583,127 | 48,767,030 | 183,904 | gain | CNVs that are Singletons |
| SK0326-003 (81155) | M | SPX | 15 | 97,406,000 | 97,961,522 | 555,523 | gain | CNVs that are Singletons |
| SK0281-003 (72934) | M | SPX | 16 | 57,542,779 | 57,579,900 | 37,122 | loss | CNVs that are Singletons |
| MM0310-005 (60951) | M | MPX | 16 | 80,972,252 | 80,983,135 | 10,884 | loss | CNVs that are Singletons |
| SK0203-004 (56040) | M | MPX | 16 | 82,603,600 | 82,687,900 | 84,300 | gain | CNVs that are Singletons |
| SK0085-004 (30422) | M | MPX | 17 | 3,836,592 | 3,998,867 | 162,276 | gain | CNVs that are Singletons |
| SK0298-003 (77697) | M | SPX | 17 | 76,914,079 | 77,771,141 | 857,063 | gain | CNVs that are Singletons |
| SK0328-003 (82302) | M | SPX | 18 | 13,794,043 | 14,743,900 | 949,858 | gain | CNVs that are Singletons |
| SK0303-003 (78391) | F | MPX | 18 | 28,383,551 | 28,448,100 | 64,550 | loss | CNVs that are Singletons |
| SK0014-003 (41606) | M | SPX | 18 | 52,531,252 | 53,165,421 | 634,169 | gain | CNVs that are Singletons |
| SK0121-003 (41288) | M | SPX | 19 | 33,693,363 | 33,762,805 | 69,442 | loss | CNVs that are Singletons |
| NA0111-000 (73891) | M | SPX | 19 | 57,836,600 | 58,246,200 | 409,601 | gain | CNVs that are Singletons |
| NA0004-000 (47490) | M | SPX | 19 | 58,634,965 | 58,958,584 | 323,620 | gain | CNVs that are Singletons |
| NA0070-000 (64249L) | F | SPX | 19 | 60,499,398 | 60,742,656 | 243,259 | loss | CNVs that are Singletons |
| SK0047-003 (47173L) | F | SPX | 19 | 61,910,800 | 62,644,900 | 734,100 | loss | CNVs that are Singletons |
| NA0110-000 (72165) | M | SPX | 19 | 63,050,356 | 63,193,800 | 143,445 | loss | CNVs that are Singletons |
| SK0232-003 (59838) | M | MPX | 19 | 63,483,000 | 63,771,100 | 288,100 | gain | CNVs that are Singletons |
| MM0018-003 (59980) | M | MPX | 20 | 11,319,093 | 11,424,900 | 105,808 | loss | CNVs that are Singletons |
| SK0335-003 (72815) | F | CHR | 20 | 14,955,730 | 15,011,214 | 55,485 | loss | CNVs that are Singletons |
| SK0258-004 (67930) | M | SPX | 20 | 45,468,000 | 45,673,300 | 205,300 | gain | CNVs that are Singletons |
| MM0126-003 (54581) | M | MPX | 21 | 22,839,570 | 22,938,377 | 98,808 | loss | CNVs that are Singletons |
| SK0118-003 (52027) | M | SPX | 21 | 28,060,406 | 28,250,400 | 189,995 | loss | CNVs that are Singletons |
| SK0186-004 (52964) | M | SPX | X | 22,962,800 | 23,119,000 | 156,200 | loss | CNVs that are Singletons |
| MM0087-003 (59962L) | M | MPX | X | 25,516,263 | 25,620,400 | 104,138 | loss | CNVs that are Singletons |
| NA0100-000 (70601L) | M | SPX | X | 44,395,900 | 45,060,800 | 664,901 | gain | CNVs that are Singletons |
| SK0087-003 (60692L) | F | MPX | X | 83,866,300 | 92,175,100 | 8,308,800 | loss | CNVs that are Singletons |
| MM0020-004 (47838) | M | MPX | X | 87,452,050 | 87,595,200 | 143,151 | gain | CNVs that are Singletons |
| SK0228-003 (62083) | M | SPX | X | 104,153,000 | 104,638,000 | 485,000 | gain | CNVs that are Singletons |
| SK0088-003 (64798) | M | SPX | X | 114,042,922 | 114,215,435 | 172,513 | gain | CNVs that are Singletons |
| MM0087-003 (59962L) | M | MPX | X | 130,406,000 | 130,695,499 | 289,500 | gain | CNVs that are Singletons |
| NA0016-000 (51524L) | F | SPX | X | 140,600,370 | 140,907,495 | 307,125 | gain | CNVs that are Singletons |
| SK0234-003 (64340) | M | SPX | X | 142,561,900 | 142,682,000 | 121,000 | loss | CNVs that are Singletons |
| SK0320-003 (79449) | M | MPX | X | 143,059,574 | 143,399,300 | 339,727 | gain | CNVs that are Singletons |
| SK0123-004 (60536L) | M | MPX | X | 147,974,000 | 148,479,449 | 505,449 | gain | CNVs that are Singletons |
| SK0278-003 (74431) | M | SPX | 1 | 188,543,244 | 188,935,335 | 392,092 | gain | CNVs that overlap the ACRD |
| MM0149-003 (42382) | M | MPX | 1 | 191,030,551 | 191,223,110 | 192,560 | gain | CNVs that overlap the ACRD |
| SK0229-003 (62211) | M | SPX | 1 | 242,451,000 | 243,113,489 | 662,489 | gain | CNVs that overlap the ACRD |
| NA0016-000 (51524L) | F | SPX | 1 | 243,172,012 | 243,301,056 | 129,044 | gain | CNVs that overlap the ACRD |
| MM0063-003 (46687) | F | MPX | 2 | 50,780,202 | 50,859,200 | 78,999 | loss | CNVs that overlap the ACRD |
| SK0234-003 (64340) | M | MPX | 2 | 54,171,783 | 54,345,700 | 173,917 | gain | CNVs that overlap the ACRD |
| SK0188-003 (53664) | M | SPX | 2 | 112,415,581 | 112,510,212 | 94,632 | loss | CNVs that overlap the ACRD |
| MM0019-003 (42052) | M | MPX | 2 | 201,286,000 | 201,317,066 | 31,067 | loss | CNVs that overlap the ACRD |
| MM0296-003 (47829) | M | MPX | 2 | 221,429,610 | 221,551,000 | 121,391 | loss | CNVs that overlap the ACRD |
| NA0004-000 (47490) | M | SPX | 2 | 235,797,267 | 236,239,000 | 441,734 | gain | CNVs that overlap the ACRD |
| MM0068-003 (60836) | M | MPX | 3 | 1,720,948 | 1,795,234 | 74,287 | gain | CNVs that overlap the ACRD |
| NA0067-000 (65344L) | M | SPX | 3 | 61,075,295 | 61,581,100 | 505,806 | gain | CNVs that overlap the ACRD |
| MM0296-003 (47829) | M | MPX | 4 | 328,851 | 542,862 | 214,012 | gain | CNVs that overlap the ACRD |
| MM0228-004 (47602) | M | MPX | 4 | 11,820,924 | 11,983,053 | 162,130 | loss | CNVs that overlap the ACRD |
| NA0129-003 (77405) | M | SPX | 4 | 38,109,899 | 38,349,444 | 239,546 | gain | CNVs that overlap the ACRD |
| SK0188-003 (53664) | M | SPX | 4 | 61,408,094 | 61,758,800 | 350,707 | loss | CNVs that overlap the ACRD |
| SK0057-003 (40919) | M | SPX | 4 | 74,105,700 | 74,464,300 | 358,600 | gain | CNVs that overlap the ACRD |
| MM0176-003 (62118L) | M | MPX | 4 | 91,220,121 | 91,309,602 | 89,482 | loss | CNVs that overlap the ACRD |
| SK0012-003 (58468L) | M | SPX | 4 | 162,387,402 | 163,362,655 | 975,254 | gain | CNVs that overlap the ACRD |
| SK0012-003 (58468L) | M | SPX | 4 | 173,324,616 | 174,954,056 | 1,629,441 | gain | CNVs that overlap the ACRD |
| SK0166-003 (36773) | M | SPX | 4 | 186,788,000 | 187,118,000 | 330,001 | gain | CNVs that overlap the ACRD |
| SK0074-003 (60910L) | M | MPX | 4 | 188,230,567 | 190,154,000 | 1,923,434 | gain | CNVs that overlap the ACRD |
| SK0083-003 (50800L) | M | CHR | 4 | 188,232,000 | 188,253,314 | 21,315 | gain | CNVs that overlap the ACRD |
| MM0019-003 (42052) | M | MPX | 4 | 190,172,765 | 191,306,043 | 1,133,279 | gain | CNVs that overlap the ACRD |
| SK0188-003 (53664) | M | SPX | 5 | 13,832,700 | 14,237,600 | 404,901 | gain | CNVs that overlap the ACRD |
| NA0078-000 (63727) | M | MPX | 5 | 79,336,190 | 79,613,516 | 277,327 | loss | CNVs that overlap the ACRD |
| NA0145-000 (82058L) | M | SPX | 5 | 89,445,869 | 90,172,900 | 727,032 | gain | CNVs that overlap the ACRD |
| SK0167-003 (60966L) | F | MPX | 5 | 120,343,925 | 120,474,000 | 130,076 | gain | CNVs that overlap the ACRD |
| NA0019-000 (64122L) | M | SPX | 5 | 120,964,000 | 121,095,213 | 131,214 | gain | CNVs that overlap the ACRD |
| MM0215-004 (47095) | M | MPX | 5 | 132,619,430 | 132,732,003 | 112,574 | loss | CNVs that overlap the ACRD |
| SK0073-003 (57283L) | F | CHR | 5 | 134,426,000 | 134,519,000 | 93,000 | gain | CNVs that overlap the ACRD |
| SK0272-003 (70721) | F | SPX | 6 | 77,622,920 | 77,673,932 | 51,012 | loss | CNVs that overlap the ACRD |
| MM0225-004 (60826) | M | MPX | 6 | 93,087,482 | 98,011,900 | 4,924,419 | gain | CNVs that overlap the ACRD |
| SK0077-003 (48226) | M | SPX | 6 | 95,461,800 | 95,581,304 | 119,504 | loss | CNVs that overlap the ACRD |
| SK0087-003 (40450) | M | SPX | 6 | 97,566,274 | 97,658,527 | 92,253 | loss | CNVs that overlap the ACRD |
| SK0216-003 (58875) | M | SPX | 6 | 153,519,631 | 153,791,029 | 271,398 | gain | CNVs that overlap the ACRD |
| NA0061-000 (60383) | M | SPX | 7 | 108,357,049 | 108,597,525 | 240,477 | loss | CNVs that overlap the ACRD |

TABLE 3-continued

| FAM ID (DNA) | Sex | Type | Chr | start | stop | size | CNV | CNV Category |
|---|---|---|---|---|---|---|---|---|
| SK0226-005 (61360) | M | SPX | 7 | 118,462,717 | 118,679,189 | 216,473 | loss | CNVs that overlap the ACRD |
| MM0218-004 (45553) | M | MPX | 8 | 89,598,961 | 89,678,800 | 79,840 | loss | CNVs that overlap the ACRD |
| SK0210-004 (57601) | M | MPX | 9 | 28,577,800 | 29,218,800 | 641,000 | loss | CNVs that overlap the ACRD |
| SK0273-003 (71182) | M | MPX | 9 | 70,739,231 | 70,870,084 | 130,854 | loss | CNVs that overlap the ACRD |
| SK0118-003 (52027) | M | SPX | 9 | 111,652,000 | 112,212,452 | 560,453 | gain | CNVs that overlap the ACRD |
| NA0066-000 (64119L) | M | SPX | 9 | 116,528,784 | 116,612,329 | 83,546 | loss | CNVs that overlap the ACRD |
| SK0102-004 (31899) | M | SPX | 10 | 42,611,900 | 43,266,300 | 654,400 | gain | CNVs that overlap the ACRD |
| SK0102-004 (31899) | M | SPX | 10 | 44,988,900 | 45,468,800 | 479,900 | gain | CNVs that overlap the ACRD |
| NA0109-000 (72873) | M | SPX | 10 | 112,267,330 | 112,405,408 | 138,079 | gain | CNVs that overlap the ACRD |
| SK0131-003 (39989) | F | CHR | 10 | 128,501,014 | 128,592,091 | 91,078 | gain | CNVs that overlap the ACRD |
| NA0138-000 (81816L) | M | SPX | 10 | 133,285,000 | 133,604,999 | 320,000 | gain | CNVs that overlap the ACRD |
| NA0113-000 (82366L) | M | SPX | 11 | 9,984,119 | 10,667,800 | 683,682 | loss | CNVs that overlap the ACRD |
| SK0218-003 (60340) | F | CHR | 12 | 1,760,084 | 1,852,412 | 92,328 | loss | CNVs that overlap the ACRD |
| NA0122-000 (76018L) | F | SPX | 13 | 32,965,700 | 33,137,655 | 171,956 | gain | CNVs that overlap the ACRD |
| NA0117-000 (73621) | M | SPX | 13 | 42,511,458 | 42,599,200 | 87,743 | gain | CNVs that overlap the ACRD |
| MM0154-003 (56678L) | F | MPX | 13 | 54,651,953 | 55,025,229 | 373,277 | gain | CNVs that overlap the ACRD |
| SK0328-003 (82302) | M | SPX | 13 | 103,896,769 | 103,930,492 | 33,724 | loss | CNVs that overlap the ACRD |
| MM0295-003 (46488) | M | MPX | 13 | 113,361,712 | 113,646,000 | 284,289 | gain | CNVs that overlap the ACRD |
| SK0305-004 (78621) | F | SPX | 14 | 42,022,286 | 42,210,026 | 187,741 | loss | CNVs that overlap the ACRD |
| SK0320-003 (79449) | M | MPX | 14 | 45,537,581 | 45,653,418 | 115,838 | loss | CNVs that overlap the ACRD |
| MM0225-004 (60826) | M | MPX | 14 | 83,373,278 | 83,435,200 | 61,923 | gain | CNVs that overlap the ACRD |
| MM0154-003 (56678L) | F | MPX | 14 | 106,223,861 | 106,356,482 | 132,622 | gain | CNVs that overlap the ACRD |
| NA0064-000 (63582L) | M | SPX | 15 | 82,573,421 | 83,631,697 | 1,058,276 | loss | CNVs that overlap the ACRD |
| MM0256-004 (46991) | M | MPX | 15 | 87,922,400 | 87,993,909 | 71,510 | gain | CNVs that overlap the ACRD |
| SK0266-003 (68257) | M | SPX | 16 | 6,813,789 | 6,898,849 | 85,060 | loss | CNVs that overlap the ACRD |
| NA0063-000 (60351) | M | SPX | 16 | 73,397,667 | 73,657,067 | 259,400 | loss | CNVs that overlap the ACRD |
| NA0095-000 (75414L) | M | SPX | 16 | 74,576,356 | 74,613,000 | 36,645 | loss | CNVs that overlap the ACRD |
| SK0284-003 (72687) | F | SPX | 17 | 28,985,300 | 29,960,700 | 975,400 | gain | CNVs that overlap the ACRD |
| SK0012-003 (58468L) | M | SPX | 18 | 27,565,032 | 27,781,900 | 216,869 | gain | CNVs that overlap the ACRD |
| SK0152-003 (41548L) | M | CHR | 18 | 32,174,061 | 32,990,975 | 816,914 | loss | CNVs that overlap the ACRD |
| SK0147-003 (47544L) | F | SPX | 18 | 37,509,556 | 37,950,450 | 440,895 | gain | CNVs that overlap the ACRD |
| SK0304-003 (78063) | M | SPX | 18 | 46,101,841 | 46,218,000 | 116,160 | gain | CNVs that overlap the ACRD |
| NA0138-000 (81816L) | M | SPX | 18 | 69,282,461 | 69,330,584 | 48,124 | loss | CNVs that overlap the ACRD |
| SK0023-003 (58096) | M | SPX | 21 | 46,497,675 | 46,678,820 | 181,145 | gain | CNVs that overlap the ACRD |
| NA0112-000 (72340) | M | SPX | X | 38,250,331 | 38,371,333 | 121,003 | gain | CNVs that overlap the ACRD |
| SK0283-003 (72309) | F | CHR | 4 | 44,762,996 | 44,858,504 | 95,508 | gain | CNVs that overlap the ACRD |
| MM0010-005 (47372) | M | MPX | 4 | 44,773,367 | 44,846,800 | 73,434 | gain | CNVs that overlap the ACRD |
| NA0093-000 (66999) | M | SPX | 4 | 44,773,367 | 44,846,800 | 73,433 | gain | CNVs that overlap the ACRD |
| MM0109-003 (46486) | F | SPX | 4 | 189,538,747 | 189,825,000 | 286,254 | gain | CNVs that overlap the ACRD |
| SK0112-003 (46100) | M | MPX | 4 | 189,580,553 | 190,228,000 | 647,447 | gain | CNVs that overlap the ACRD |

Figure 3:
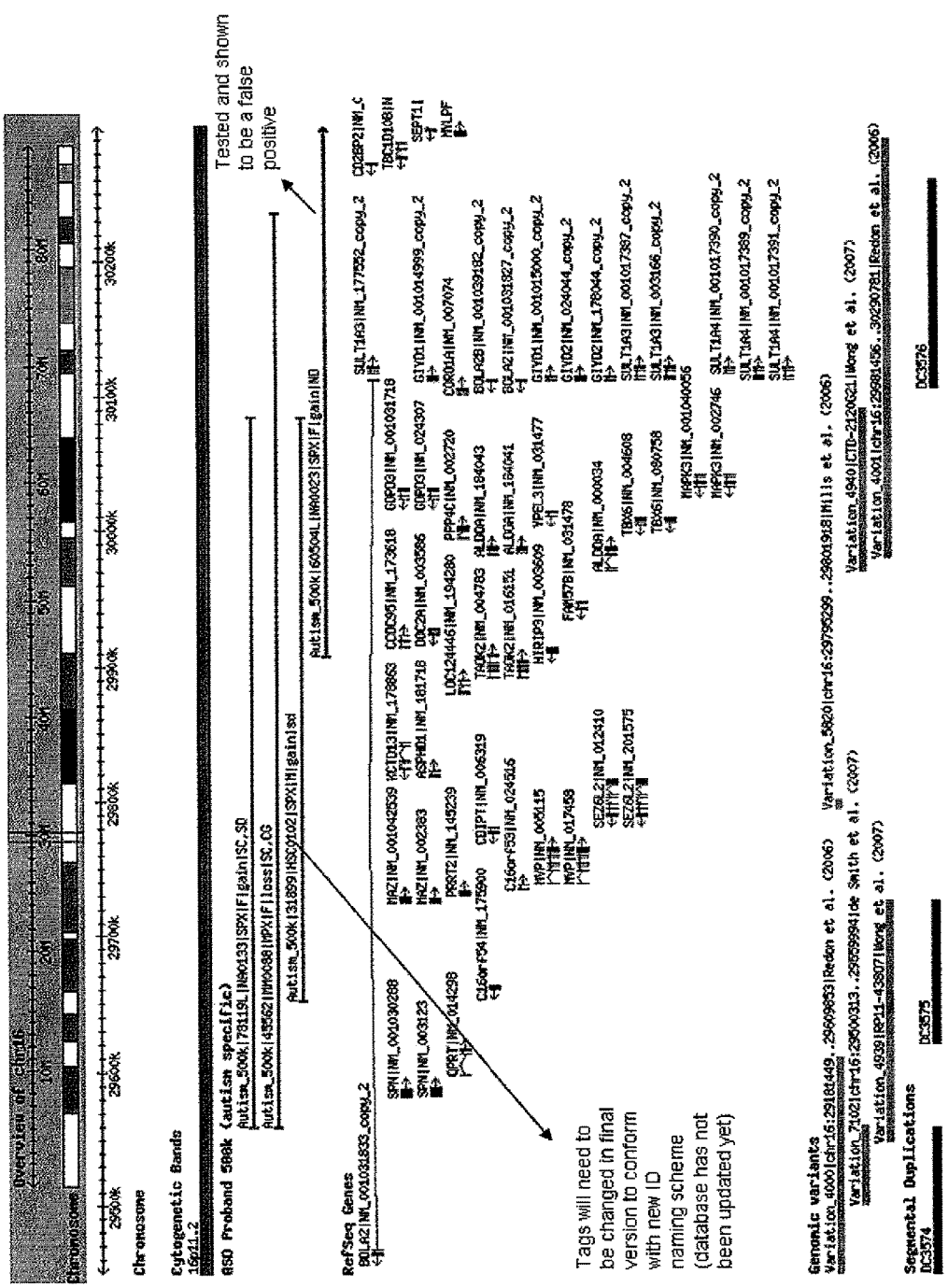
FIG. 3 illustrates the chromosome 16p11.2 region as depicted in the Autism Chromosome Rearrangement Database.

Wide-ranging prevalence frequencies of cytogenetically detectable chromosomal abnormalities in ASD, and the inability of microarray scans to find balanced abnormalities, prompted karyotyping to be performed. Karyotyping (and FISH) also provided the ability to characterize the chromosomal context (e.g. ring chromosomes) of some of the CNV regions, something not possible using microarrays alone. Therefore, 313 unbiased idiopathic cases where blood was available were examined and 5.8% (18/313) cases were found to have balanced (11) or unbalanced (7) karyotypes (all unbalanced karyotypic changes (7) were also found by microarray analysis and are included in the CNV statistics). The genomic characteristics of all CNVs are shown in the Autism Chromosome Rearrangement Database (see FIG. 3). In this study, CNV loss and gain will typically equate to a standard deletion or duplication. In some cases a duplication of only part of a gene could lead to its disruption (Table 5), and there are also positional effects on gene expression to consider.

De Novo, Overlapping/Recurrent, and Inherited Structural Variants

Structural variants found in ASD cases were initially prioritized to possibly be etiologic if they were not in controls and, (i) de novo in origin (25 cases) (see Table 5 below), (ii) overlapping (27 cases at 13 loci) in two or more unrelated samples (see Table 7 below), (iii) recurrent (same breakpoints) in two or more unrelated samples (four cases at two loci), (iv) or inherited the remainder). In a proof of principle analysis, CNVs were found at known ASD loci: NLGN4 and 22q, 15q, SHANK3 and NRXN1 in categories i, ii, iii, and iv, respectively. ASD structural variants found in controls (eg. NRX1) could also be involved.

TABLE 5

De Novo Rearrangements in ASD cases

| | FamID (DNA)[1] | Sex | Type | Chromosome[2] | Size (bp)[3] | CNV | Genes[4] | Phenotype Comments[5] |
|---|---|---|---|---|---|---|---|---|
| 1 | SK0181-004 (52191) | M | CHR (SPX) | 3p14.1-3p13 (a) | 5,346,900 | loss | 13 genes | IQ = 107 |
| | | | | t(6; 14)(q13; q21)(k) | N/A | none | 11 genes | Dysmorphology |
| 2 | SK0152-003 (41548) | M | CHR (MPX)[6] | 3p25.1-p24.3 (a) | 1,409,600 | loss | 12 genes | IQ = unknown |
| | | | | 5p15.31-p15.2 (a) | 3,429,389 | loss | 8 genes | |
| | | | | 12q12 (a) | 422,842 | loss | 4 genes | |
| | | | | t(5; 7)(p15p13) (k) | N/A | none | CDH18 | |
| 3 | SK0215-006 (58449) | M | CHR (SPX) | 1p21.3 (a) | 1,092,500 | loss | DPYD whole | IQ = 38, SLI |
| 4 | SK0205-004 (56242) | F | CHR (SPX) | 5p15.33-5p15.2 (k) | 13,800,984 | loss | 46 genes | IQ = unknown, Cri du chat |

TABLE 5-continued

De Novo Rearrangements in ASD cases

| | FamID (DNA)[1] | Sex | Type | Chromosome[2] | Size (bp)[3] | CNV | Genes[4] | Phenotype Comments[5] |
|---|---|---|---|---|---|---|---|---|
| 5 | SK0083-003 (50800) | M | CHR (SPX) | 7q31.1-q31.31 (k) | 11,023,507 | loss | 25 genes | IQ = 76 |
| 6 | SK0131-003 (39989) | F | CHR (SPX) | 7q31.1-q32.2 (k) | 15,486,722 | loss | >50 genes | IQ = 95, SLI |
| 7 | SK0243-003 (67941) | M | CHR (SPX) | 15q23-q24.2 (k) | 4,289,500 | loss | >50 genes | IQ = unknown, SLI |
| 8 | SK0073-003 (57283) | F | CHR (SPX) | 15q11.2-q13.3 (k) | 11,922,600 | gain | >50 genes | IQ = unknown |
| 9 | SK0245-005 (68517) | M | CHR (SPX) | 15q11.2-q13.3 (k) | 11,871,747 | gain | >50 genes | IQ = unknown |
| 10 | SK0218-003 (60340) | F | CHR (MPX)[4] | 18q21.32-18q23 (k) | 20,358,999 | loss | >50 genes | IQ = unknown, seizures, dysmorphology |
| 11 | NA0039-000 (69736) | F | CHR (SPX) | 22q13.31-q13.33 (k) | 3,231,700 | loss | 41 genes | IQ = unknown |
| 12 | NA0097-000 (82361) | F | CHR (SPX) | Xp22.33-p22.31 (a) | 5,825,311 | loss | 21 genes + NLGN4 | IQ = unknown |
| 13 | SK0283-003 (72309) | F | CHR (SPX) | 47, XX, ring chr1 (k) | N/A | gain | >50 genes | IQ = 38 |
| 14 | SK0133-003 (46012) | M | CHR (SPX) | t(5; 8; 17)(q31.1; q24.1; q21.3) (k) | N/A | none | 5 genes | IQ = unknown |
| 15 | NA0002-000 (52026) | M | SPX | 7q36.2 (a) | 66,462 | loss | DPP6 exonic | IQ = unknown |
| 16 | SK0262-003 (68609) | M | SPX | 8p23.3 (a) | 791,089 | gain | DLGAP2 exonic | IQ = unknown |
| 17 | MM0278-003 (57788) | M | SPX | 12q24.21-q24.33 (a) | 18,218,000 | gain | >50 genes | IQ = 36 |
| 18 | NA0067-000 (65344) | M | SPX | 16q24.3 (a) | 265,667 | loss | ANKRD11 exonic | IQ = unknown |
| 19 | MM0088-003 (45562) | F | MPX | 16p11.2 (a) | 675,829 | loss | 28 genes | IQ = 87 |
| 20 | SK0102-004 (31899) | M | SPX | 16p11.2 (a) | 432,600 | gain | 24 genes | IQ = 74, Epilepsy |
| 21 | SK0244-003 (69183) | M | SPX | 21q22.3 (a) | 353,936 | gain | 4 genes | IQ = 80 |
| 22 | MM0109-003 (46486) | F | SPX | 20q13.33 (a) | 1,427,661 | gain | 44 genes | IQ = unknown |
| | | | | 22q13.33 (a) | 276,702 | loss | 13 genes + SHANK3 | |
| 23 | SK0119-003 (35190) | M | MPX[4] | 22q11.21 (a) | 2,771,300 | loss | >50 genes | IQ = 58, VCF syndrome |
| 24 | SK0297-003 (76066) | M | SPX-MZ | 22q11.21 (a) | 4,281,262 | gain | >50 genes | IQ = 107, dysmorphology |
| 25 | SK0306-004 (78681) | F | SPX | Xp11.23-11.22 (a) | 4,643,367 | gain | >50 genes | IQ = 87 |

[1]Table is sorted based on family type. Probands with abnormal karyotypes (CHR) (1-14) are separated from probands belonging to simplex (SPX) and multiplex (MPX) families with normal karyotypes (15-25).
[2]De novo event detected by either karyotype (k) or microarray (a)
[3]De novo CNV/translocation has been confirmed by at least one of karyotype, FISH, or qPCR. CNV size is based on array results. The breakpoints have not been accurately defined, and CNVs may be smaller or larger than posted.
[4]When only a single gene is involved if the CNV intersects (suggesting it may disrupt the gene) the term 'exonic' is used and if the CNV encompasses the entire gene the term 'whole' is used.
[5]For multiplex families the de novo events were not detected in affected siblings.
**comment on case 25 that is also in Table 3(see entry #2

TABLE 6

Recurrent and overlapping loci in ASD

| | Chromosome | FamID (DNA) | Sex | Type[1] | Size (bp)[2] | CNV | Origin | Genes[3] | Phenotype Comments |
|---|---|---|---|---|---|---|---|---|---|
| 1 | 2q14.1 | SK0147-003 (47544) | F | SPX | 478,370 | loss | Paternal | DPP10 exonic | IQ = unknown, NF1 |
| | | SK0288-003 (75420) | M | SPX-MZ | 105,120 | gain | Paternal | DPP10 intronic | IQ = 83 |
| 2 | 2q32.1 | SK0306-004 (78681) | F | SPX | 97,130 | loss | Unknown | None | IQ = 87 |
| | | NA0030-000 (55240) | M | SPX | 112,323 | loss | Unknown | None | IQ = unknown |
| 3 | 6q22.31 | MM0220-003 (61180) | M | MPX | 318,000 | gain | Paternal | PLN, c6orf204 whole | IQ = unknown |
| | | NA0025-000 (60490) | M | SPX | 293,989 | gain | Paternal | PLN, c6orf204 whole | IQ = unknown |
| 4 | 7q36.2 | SK0190-003 (54742) | M | SPX | 1,780,000 | gain | Maternal | DPP6 whole | IQ = 82 |
| | | SK0115-003 (40555) | M | SPX | 274,000 | gain | Unknown | DPP6 exonic | IQ = unknown |
| | | SK0058-003 (59963) | M | MPX | 16,788 | gain | Maternal | DPP6 intronic | IQ = 111 |
| | | NA0002-000 (52026) | M | SPX | 66,462 | loss | De novo | DPP6 exonic | IQ = unknown |
| 5 | 8q11.23 | SK0143-003 (36812) | M | SPX | 285,200 | gain | Unknown | UNQ9433 whole, RB1CC1 exonic | IQ = 66, Apraxia, CHD, Seizures |
| | | MM0236-004 (46475) | M | MPX | 271,679 | gain | Unknown | RS1CC1 exonic | IQ = 99 |
| 6 | 9p24.1 | SK0270-003 (71341) | M | SPX | 38,900 | loss | Unknown | none | IQ = 91, SLI |
| | | MM0103-003 (42387) | M | MPX | 34,950 | loss | Paternal | none | IQ = 107 |
| 7 | 11p12 | MM0272-003 (45563) | M | MPX | 262,938 | loss | Maternal | none | IQ = 111, Seizures |
| | | SK0167-003 (60966) | F | MPX | 192,846 | loss | Unknown | none | IQ = 91 |
| 8 | 13q21.32 | SK0023-003 (58096) | M | SPX | 189,438 | gain | Unknown | PCDH9 intronic | IQ = 91, Seizures |
| | | MM0299-003 (51674) | F | MPX | 172,401 | gain | Paternal | PCDH9 intronic | IQ = 39 |
| 9 | 15q11.2-q13.3 | SK0073-003 (57283) | F | CHR | 11,922,600 | gain | De novo | >50 genes | IQ = unknown |
| | | SK0245-005 (68517) | M | CHR | 11,871,747 | gain | De novo | >50 genes | IQ = unknown |
| 10 | 16p12.1 | MM0109-003 (46486) | F | SPX | 1,246,288 | gain | Maternal | 8 genes | IQ = unknown |
| | | MM0289-003 (42267) | F | MPX | 802,555 | loss | Maternal | 5 genes | IQ = 63 |
| 11 | 16p11.1 | NA0133-000 (78119) | F | SPX | 525,319 | gain | Maternal | 29 genes | IQ = unknown |
| | | SK0102-004 (31899) | M | SPX | 432,600[4] | gain | De novo | 24 genes | IQ = 64, Epilepsy |
| | | MM0088-003 (45562) | F | MPX | 675,829 | loss | De novo | 32 genes | IQ = 87 |
| 12 | 22q11.2 | SK0119-003 (35190) | M | MPX | 2,771,300 | loss | De novo | >50 genes | IQ = 58, VCF syndrome |
| | | SK0091-004 (46407) | F | MPX | 4,281,262 | gain | Paternal | >50 genes | IQ = 126 |
| | | SK0297-003 (76066) | M | SPX-MZ | 4,281,262 | gain | De novo | >50 genes | IQ = 107, dysmorphology |
| | | SK0323-003 (80022) | M | MPX | 743,100 | gain | Unknown | 7 genes | IQ = unknown |

TABLE 6-continued

Recurrent and overlapping loci in ASD

| | Chromosome | FamID (DNA) | Sex | Type[1] | Size (bp)[2] | CNV | Origin | Genes[3] | Phenotype Comments |
|---|---|---|---|---|---|---|---|---|---|
| 13 | 22q13.31 | SK0123-004 (60536) | M | MPX | 601,528 | gain | Maternal | none | IQ = 93 |
| | | MM0102-003 (47598) | M | MPX | 80,380 | loss | Maternal | none | IQ = 70 |

Figure 2:
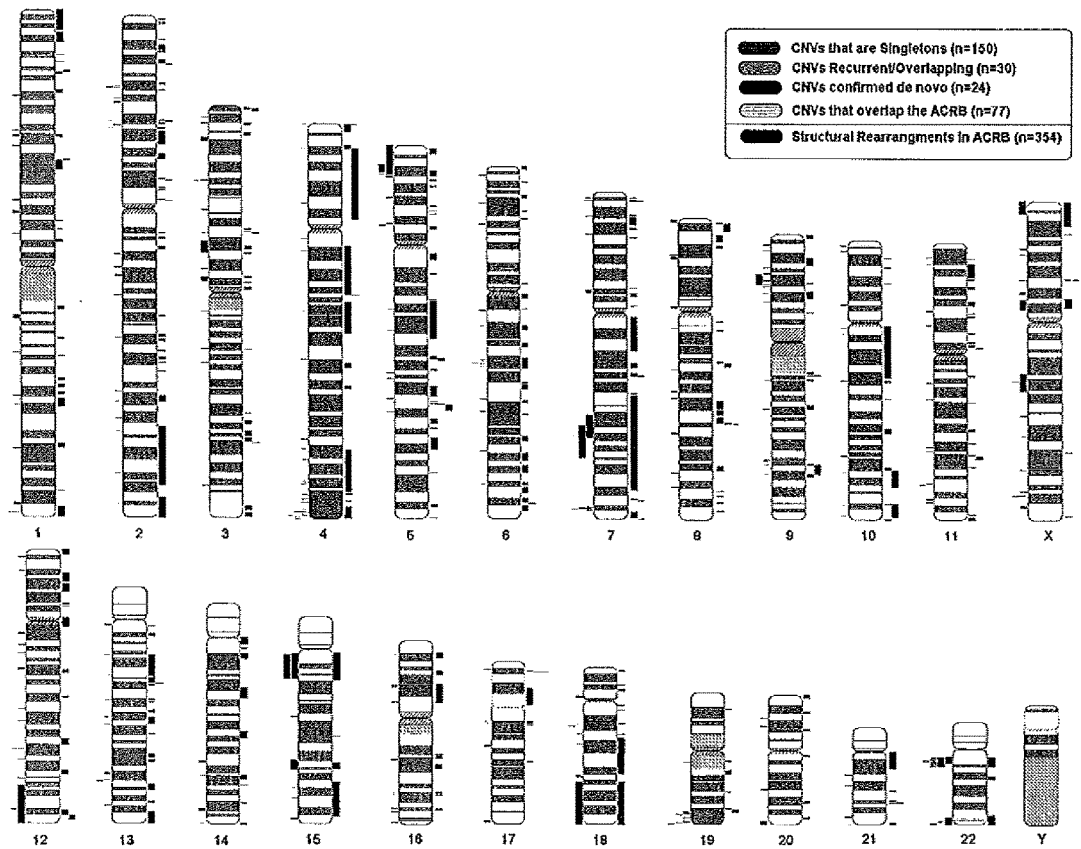
FIG. 2 illustrates a genome-wide distribution of ASD-specific CNVs as described in Table 3.

[1]Families are grouped based on simplex (SPX), multiplex (MPX) and chromosomal abnormalities (CHR). Simplex families with affected monozygotic twins is denoted as SPX-MZ. The de novo cases also appear in Table 2 and some of the family pedigrees are shown in FIG. 2 and Supplemental FIG. 2.
[2]CNV size is based on array results. The breakpoints have not been accurately defined, and CNVs may be smaller or larger than posted.
[3]When only a single gene is involved if the CNV intersects (suggesting it may disrupt the gene) the term 'exonic' is used and if the CNV encompasses the entire gene the term 'whole' is used.
[4]CNV is only called by one algorithm By testing parental DNA and validating CNVs, a de novo mutation rate of 7.1% (4/56) and 2.0% (1/49) was observed in idiopathic simplex and multiplex families, respectively. There was parental information for 13 of 18 cases discovered to carry cytogenetic abnormalities and 7 (6 simplex, 1 multiplex) of these were de novo in origin. Since only 1/7 (from a simplex family) of these was balanced and directly interrupting a gene, it was estimated that this class of rearrangements had much less of a contribution than CNVs to the total rate of de novo and structural variation in the present cohort.

The collective data identified 25 de novo cases (Table 5) and in three, two or more events were identified. Notably, in family SK0152 (FIG. 4a) there were four de novo events. In MM019 (FIG. 4b) there were two de novo deletions, one leading to haplo-insufficiency of SHANK3.

The 13 loci where overlapping ASD-specific CNVs were found are likely indicative of ASD-susceptibility since they arise in two or more unrelated families. In six, gains and losses often encompassing entire genes were observed at the same locus (Table 6) suggesting general gene dysregulation to be involved.

Using q-PCR or by assessing SNP patterns, 196 inherited CNVs (90 maternal and 106 paternal) were confirmed. No sub-grouping of these demonstrated obvious parent-of-origin effects (the two chromosome 15q11-q13 duplications detected were both de novo in origin). A 160 kb deletion was detected in a male inherited from a carrier mother, leading to a null PTCHD1 in the proband and his dizygotic twin brother (FIG. 4c). There were also instances where apparently balanced inherited translocations were accompanied by de novo deletions in the offspring (eg. DPYD) (FIG. 4d).

Candidate ASD-Susceptibility Genes and Loci Identified

New ASD candidates identified were those with a structural change (either de novo or found in two or more unrelated ASD cases, or for the X chromosome an allele being transmitted maternally from an unaffected carrier) specific to that gene, including ANKRD11, DLGAP2, DPP6, DPP10, DPYD, PCDH9 and PTCHD1 (Tables 5 and 6). As previously noted, NLGN4, SHANK3 and NRXN1 were also identified. The PCDH9 and NRXN1 genes are also found as CNVs in controls in the DGV (Database of Genomic Variants).

Additional positional candidate genes identified were those found interrupted by balanced cytogenetic breakpoints including NEGR1, PIP5K1B, GABRG1, KLHL3, STK3, ST7, SATB2 (Table 1). Moreover, 77 CNVs in the stringent dataset overlapped with the Autism Chromosome Rearrangement Database providing a second line of evidence for involvement (FIG. 2). For example, a 4.6 Mb de novo duplication at Xp11.23-11.22 was detected in a female SK0306-004 (Table 5) and a male in the database.

DPP6 and DPP10 emerge as being positional and functional candidates. DPP6 (~1.5 Mb in size at 204.1) and DPP10 (~1.3 Mb at 7q36.2) code for accessory transmembrane dipeptidyl peptidase-like subunits that affect the expression and gating of Kv4.2 channels (KCND2). Kv4.2 channels function in regulation of neurotransmitter release and neuronal excitability in the glutamatergic synapse at the same sites where SHANK3 and the NLGN gene products are found. In addition, autism balanced breakpoints have been mapped near KCND2 at 7q31.

Figure 4:
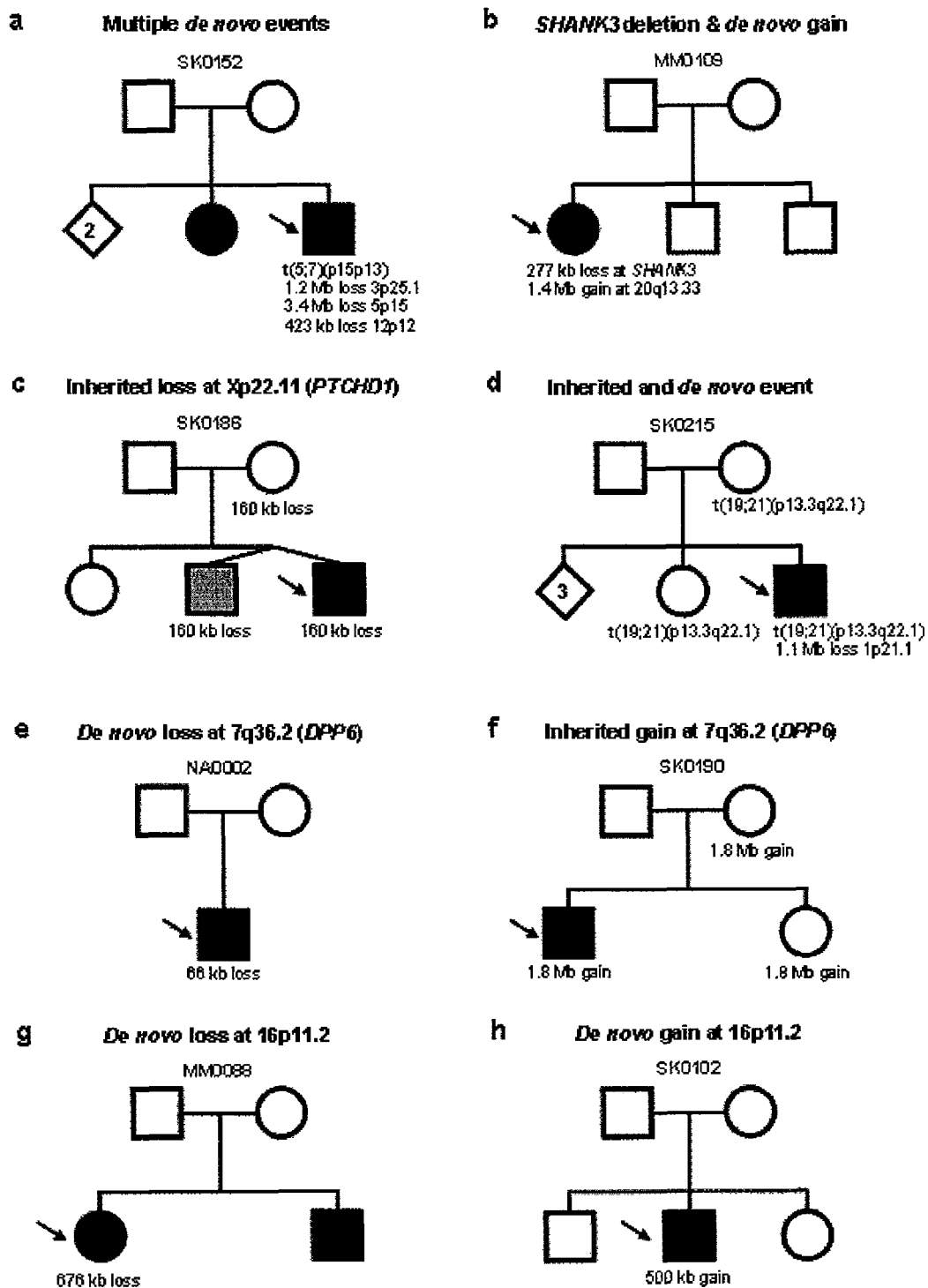
FIG. 4 illustrates examples of CNVs observed in ASD families including probands having multiple de novo events (a); rearrangements in the SHANK3 gene (b); probands with chromosome X deletions (at PTCHD1) from female carriers (c) or inherited translocations in addition to an unrelated de novo deletion (d); overlapping events in unrelated probands either de novo (e) or inherited (t) at the DPP6 locus; and recurrent de novo events at chromosome 16p11.2 in unrelated probands either gains (h) or losses (g)
Figure 5:
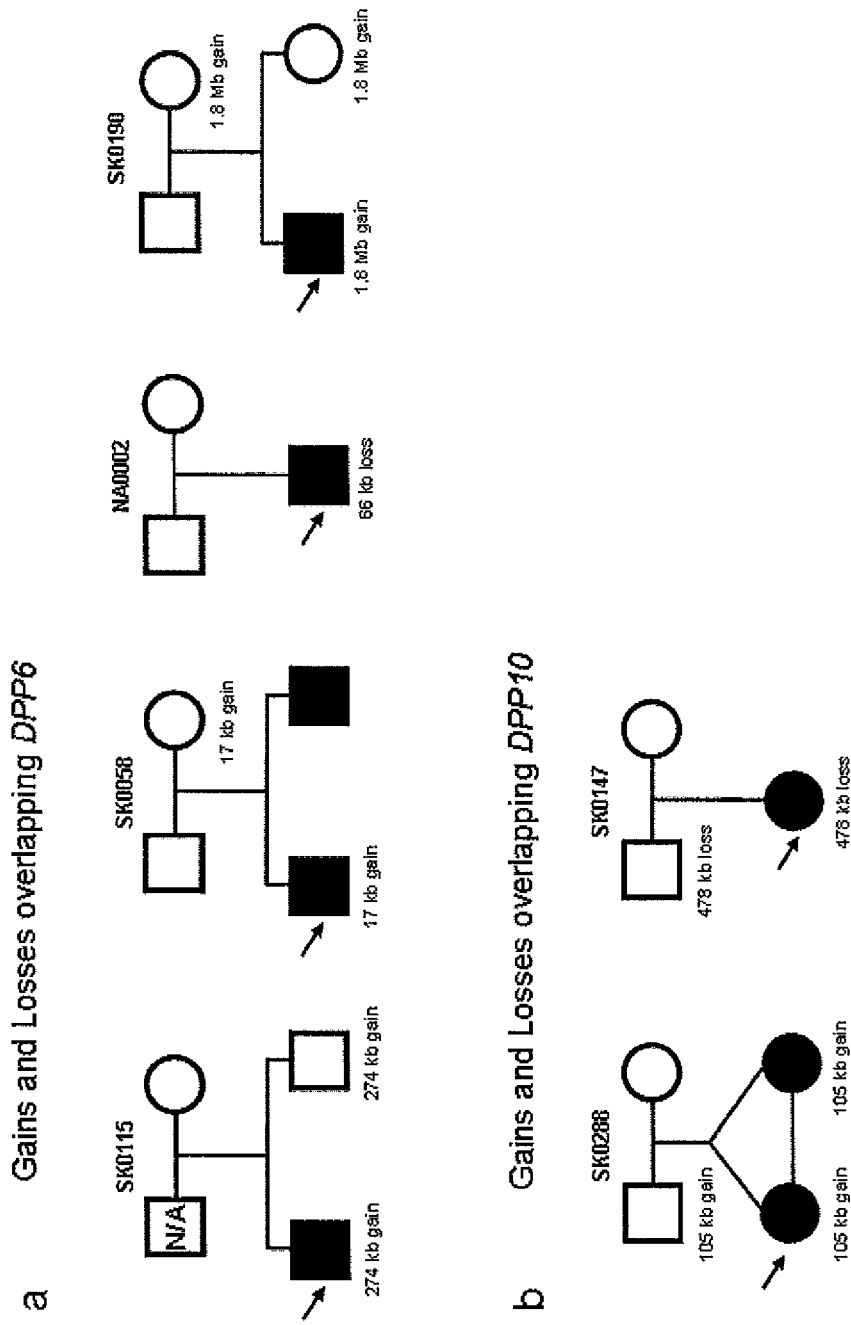
FIG. 5 illustrates examples of DPP6 and DPP10 ASD-related CNVs.

For DPP10 there are inherited CNV gains and losses (Table 5, FIG. 4). De novo and inherited CNVs were found at the multi-transcript DPP6 gene. A 66 kb de novo loss encompassing exons 2 and 3 is found in a male in family NA0002 (FIG. 4e). In family SK0190, the male proband and an unaffected female sibling both carry a CNV gain inherited from an unaffected mother (FIG. 4f) that encompassed the entire DPP6. A 270 kb gain was found in SK0115-003 that extends across the first exon (which may disrupt the functional gene) and SK0058-003 carries a maternally-inherited 16 kb intronic CNV gain (Table 1; FIG. 5).

Medical Genetics

Structural variants overlapping loci involved in medical genetic conditions including Waardenburg Type IIA (3p14.1), speech and language disorder (7q31), mental retardation (MR)(15q23-q24, 16p11.2) and velocardialfacial syndrome (VCFS) (22q13) were identified (Table 5), amongst others. Identification of the structural variant at these loci led to clinical re-assessment and either identification or refinement of the diagnosis, for additional syndromic features. Other instances (eg. SK0186-PTCHD1 deletion) (FIG. 4c) prompted re-testing of the entire family and eventually a diagnosis of mild-ASD in a previously undiagnosed sibling. This family was then redesignated multiplex as opposed to simplex.

Figure 6:
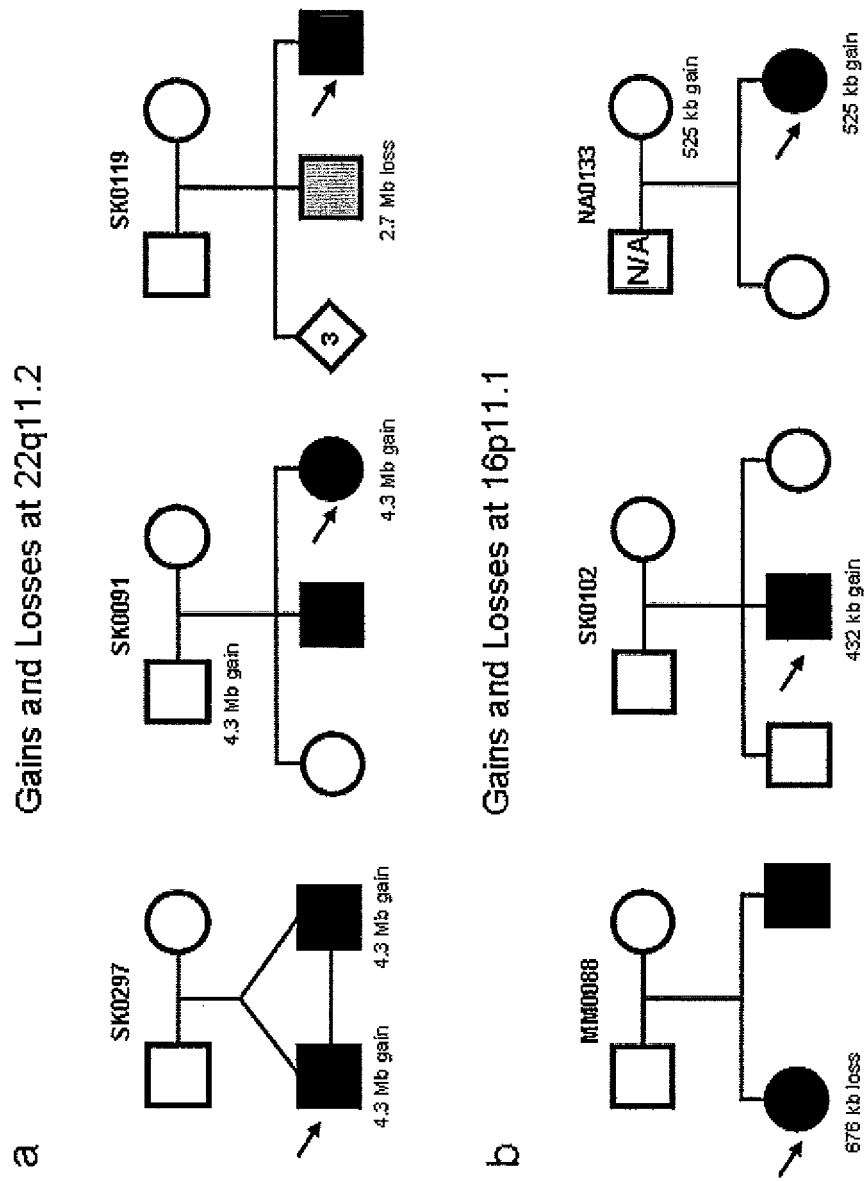
FIG. 6 illustrates examples of chromosome 22q11.2 and 16p11.2 ASD-related CNVs.

The identification of a de novo deletion (2.7 Mb) at 22q11.2 in two ASD brothers led to their re-examination and diagnosis for VCFS. The re-testing also further defined the siblings to be at opposite ends of the ASD spectrum (FIG. 6). Larger duplications (4.3 Mb) of this same region in two other ASD families (SK0289 and SK0091) did not cause VCFS (Table 6); however, in SK0091 the variant was inherited from a normal father and not found in an affected male sibling.

A recurrent ~500 kb duplication at 16p11.2 in two ASD families (SK0102 and NA0133) (FIGS. 4 and 5) was also discovered. As with DPP6/DPP10 and 22q11.2, there were carriers of these structural variants without ASD. In a third family (MM0088), the proband has a larger 676 kb de novo deletion and it is only detected in one of two ASD siblings. (FIG. 4g).

In sum, using the genome-wide scanning approach, numerous new putative-ASD loci (Tables 4 and 5, FIG. 2) were identified. Generally, ASD loci include (i) those that contain genes functioning in the PSD, (ii) and/or chromosomal regions previously shown to be involved in mental retardation, and (iii) involve dysregulation of gene expression.

CNVs that implicate ASD loci include the SHANK3, NLGN, and NRXN1-PSD genes and also identify novel loci at DPP6 and DPP10 (amongst others including PCDH9, RPS6KA2, RET from the full dataset) were identified.

Lastly, six unrelated ASD cases were identified (Table 6) that had either CNV gains or losses at the same locus which indicate that gene expression of genes in these regions are related to the development of speech and language and/or social communication in humans, as in SHANK3 and genes in the Williams-Beuren syndrome locus.

Example 2

PTCHD1 as a Marker of ASD

As set out above, a genome scan with Affymetrix 500K SNP Arrays was used to identify a CNV deletion on chromosome Xp22.11 that spans exon 1 of the PTCHD1 gene. Exon 1 is shown bolded in FIG. 7 spanning nucleotide positions 1-359. The Cdna sequence of the PTCHD1 gene (NM_173495) as well as the amino acid sequence of the corresponding encoded protein is illustrated in FIG. 7 which illustrates a genomic size of: 59325, an exon/coding exon count of 3 encoding a protein of 783 amino acids.

The deletion was determined to be an ~156 kb deletion on Xp22.11 on a male proband. The physical position of this CNV is chrX:22, 962,800-23, 119,000 (UCSC 2004 Assembly). The deletion is flanked by SNP probes rs7055928 and rs1918560 (at 22.956 and 23.133 Mb from the Xp terminus, respectively). The most proximal and distal SNPs (from the Affymetrix SNP microarrays) within the deleted region, as determined by the SNP microarray analysis, are rs7879064 (23.119 Mb) and rs4828958 (22.972 Mb). PCR amplicons from within the deleted region were used to confirm the deletion by Qpcr (PCR primers and locations are given below). This deletion spans the entire exon 1 of the PTCHD1 gene (NM_173495). Analysis of both Sty and Nsp chips data identified this event and was further validated using PCR and QPCR techniques. The following primers were used:

```
                                       (SEQ ID NO: 1)
PTCHD-CNV1F  ATTCGCAGTTCCTTCGTCTT (SEQ ID NO: 2)
PTCHD-CNV1R  AAAGTGGATTGATCGGTTCC (SEQ ID NO: 3)
PTCHD-CNV2F  GCTTGAGGACGTGTTTCTCC (SEQ ID NO: 4)
PTCHD-CNV2R  CTAGGAGAGGTGGCGCTCT
```

This CNV is autism specific as it was not present in the Database of Genomic Variants (DGV) and in other controls. Furthermore, the segregation of this deletion was characterized in family and it was identified that the deletion was transmitted from a heterozygous mother. A male sibling also had language deficits.

Mutation screening of PTCHD1 in N=400 autism patients was conducted in the usual manner. The following primers were used:

```
                                       (SEQ ID NO: 5)
PTCHD1-x1F   AGCGTGCGCCTCGCCCT (SEQ ID NO: 6)
PTCHD1-x1R   TCCTTGTCCAGGAGGCTGGGA (SEQ ID NO: 7)
PTCHD1-x1Bf  GCGCCCGCTCTGCTCTA (SEQ ID NO: 8)
PTCHD1-x1Br  TCCTTGTCCAGGAGGCTGGGA (SEQ ID NO: 9)
PTCHD1-x2-F  GAATGTCCACCCTCTCCAAA (SEQ ID NO: 10)
PTCHD1-x2-R  AAGGCTACTCCTGGCCTTTT (SEQ ID NO: 11)
PTCHD1-x3a-F CTTTGACCCAGTAGTCCCTCA (SEQ ID NO: 12)
PTCHD1-x3a-R GCACAAACCCCTTGGTGTA (SEQ ID NO: 13)
PTCHD1-x3b-F TGTGATTGGGTTTTACATATATGAGTC (SEQ ID NO: 14)
PTCHD1-x3b-R AGGTCAGATTTGAAGGCACAG (SEQ ID NO: 15)
PTCHD1-x3c-F AAAAATGCCCTGGAAGTGC (SEQ ID NO: 16)
PTCHD1-x3c-R TGTGTGAATTCTCATAACAACTCCT
```

The mutation screening revealed an I173V mutation.

Example 3

Identification of Additional Markers of ASD

Figure 8:
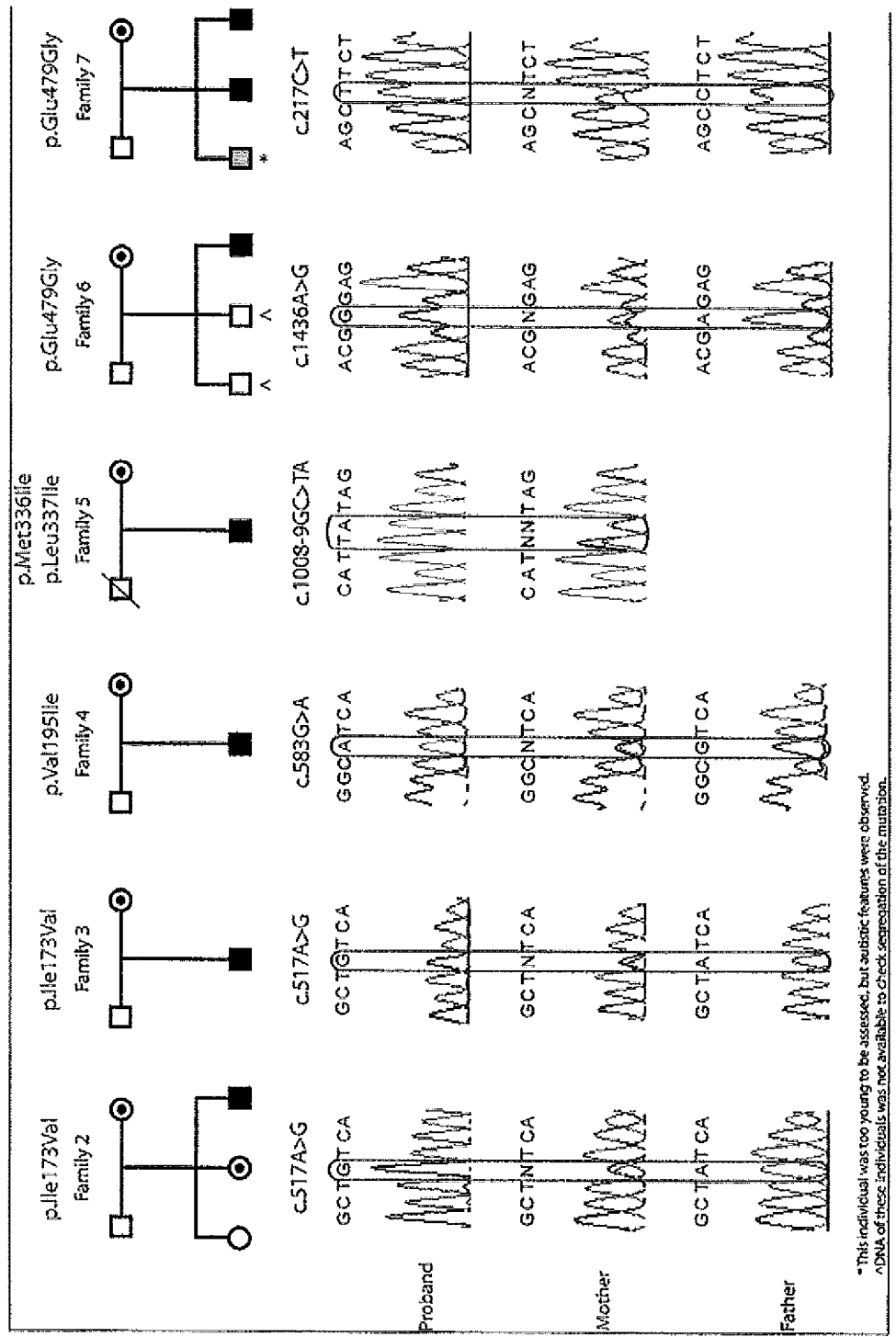
FIG. 8 illustrates ASD-related missense mutations identified in Table 7.

By sequencing the entire coding region of PTCHD1 in 900 unrelated ASD cases, six missense mutations were identified in six unrelated ASD probands (Table 7, FIG. 8). For clinical details see Table 8.

TABLE 7

| Subject ID | Exon | Mutation | Nucleotide | Sex of Proband | Transmission | Family Type | XCI Status of Carrier Mother | Population Ancestry | Frequency in ASD | No. of Control Chromosomes Tested |
|---|---|---|---|---|---|---|---|---|---|---|
| Family 1 | 1 | 167-kb deletion, disrupts PTCHD1 gene at Xp22.11 | | M | Mother | Multiplex | Skewed | European | 1 in 427 | 2067 (M = 769 F = 1298) |
| Family 1 | 1 | 167-kb deletion, disrupts PTCHD1 gene at Xp22.11 | | M | Mother | Multiplex | Skewed | European | 1 in 427 | 2067 (M = 769 F = 1298) |

TABLE 7-continued

| Subject ID | Exon | Mutation | Nucleotide | Sex of Proband | Transmission | Family Type | XCI Status of Carrier Mother | Population Ancestry | Frequency in ASD | No. of Control Chromosomes Tested |
|---|---|---|---|---|---|---|---|---|---|---|
| Family 2 | 2 | I173V | 517A > G | M | Mother | Multiplex | Random | European\Mixed | 2 in 900 | 659 (M = 219 F = 220) |
| Family 3 | 2 | I173V | 517A > G | M | Mother | Simplex | Random | European | 2 in 900 | 659 (M = 219 F = 220) |
| Family 4 | 2 | V195I | 583G > A | M | Mother | Simplex | NC | European | 1 in 900 | 659 (M = 219 F = 220) |
| Family 5 | 2 | ML336-7II | 1008-9GC > TA | M | Mother | Simplex | Random | Asian | 1 in 900 | 751* (M = 249 F = 251) |
| Family 6 | 3 | E479G | 1436A > G | M | Mother | Multiplex | Random | European | 1 in 900 | 427 (M = 137 F = 145) |
| Family 7 | 1 | L73F | 217C > T | M | Mother | Multiplex | NC | Not Available | 1 in 900 | 427 (M = 137 F = 145) |

*Out of 751 control chromosomes tested, N = 92 were Asian

TABLE 8

| Subject ID | Sex | Mutations | Clinical Details | Family History | Comments |
|---|---|---|---|---|---|
| Family 1 | M | 167-kb del | Meet ADI and ADOS-1 criteria for diagnosis of autism. Difficulty with conversations, echoed words, repetitive interests, delay in social use of language. Attention Deficit and Hyperactivity Disorder (ADHD). No mental retardation (MR). Non-Verbal IQ = 42% ile | Maternal history of learning problem and articulation difficulties. Paternal history of ADHD like features. | Severe colic during early childhood |
| Family 1 | M | 167-kb del | Meet ADI and ADOS-1 criteria for diagnosis of autism. Difficulty with conversations, echoed words, repetitive interests, delay in social use of language. Attention Deficit and Hyperactivity Disorder (ADHD). No mental retardation (MR). Non-Verbal IQ = 23% ile | Maternal history of learning problem and articulation difficulties. Paternal history of ADHD like features. | Severe colic during early childhood |
| Family 2 | M | I173V | Meet ADI and ADOS-1 criteria for diagnosis of autism. Highly repetitive language and behaviour, motor mannerisms, extremely hyperactive, poor motor coordination and mental retardation, Lang: receptive = 40, <1% ile, expressive = 40, <1% ile | Father had type II diabetes | |
| Family 3 | M | I173V | Meet ADI and ADOS-1 criteria for diagnosis of autism. Meet ADI and ADOS-1 criteria for diagnosis of autism. ADI social score = 25, ADI communication score = 21, ADI Restricted, Repetitive, and Stereotyped Behavior Score = 11, ADI development score = 3, Normal IQ, | No family history of PDD | |
| | M | V195I | Diagnosed with autism at the age of 3 years and 4 months. Meet ADI and ADOS-1 criteria for diagnosis of autism. Severe expressive and receptive language delay. No dysmorphology observed. | No family history of PDD | FRX and head CT scan was normal |
| Family 5 | M | ML336-7II | Meet ADI and ADOS-1 criteria for diagnosis of autism. ADI social score = 26, ADI communication score = 14, ADI stereotype score = 5 ADI development score: 4, ADOS social + communication score = 20, ADOS Restricted, Repetitive, and Stereotyped Behavior Score = 3, Some traits were observed that could be related to schizophrenia. | Father died of leukemia | Minor thalassemia |
| Family 6 | M | E479G | Diagnosed with high functioning autism. | No family history of PDD | |
| Family 7 | M | L73F | Meet ADI and ADOS-1 criteria for diagnosis of autism | | |

All these mutations resulted in the substitution of highly conserved amino acids, and were inherited from unaffected carrier mothers. Based on in silico protein modeling, three mutations (L73F, I173V, V195I) are present in a predicted amino acid loop that sits outside of the cell membrane. This loop is posited to interact with the ligand, Hh. Another mutation, the 2-amino acid substitution ML336-337II was present within a predicted transmembrane domain. Finally, the E479G mutation was present within a predicted cytoplasmic amino acid loop. In five out of six families, these mutations segregated with the phenotype. Controls (439) were tested for the I173V and V195I mutations, 500 controls for ML336-337II, and 282 controls for L73F and E479G. None of these mutations were present in controls. Furthermore, the fact that these mutations were all maternally inherited to male probands, and were not observed in our control populations, indicates that the mutations are associated with ASD. In turn, it is reasonable to assume that these mutations contribute to the etiology of autism, and perhaps in-combination with other disease-related loci, give rise to the ASD phenotype.

Interestingly, in two of the ASD families reported in Tables 7/8 (Family-2 & Family-4), other ASD-related CNVs were identified. In family 2, in addition to I173V mutation, a de novo ~1.0 Mb loss at 1p21.3 resulting in deletion of the entire DPYD gene (NM_000110.3) was identified. DPYD encodes a rate-limiting enzyme, dihydropyrimidine dehydrogenase (DPD), involved in pyrimidine metabolism.

Complete DPD deficiency results in highly variable clinical outcomes, with convulsive disorders, motor retardation, and mental retardation being the most frequent manifestations. In Family-4, in addition to the V195I mutation, a 66 Kb de novo loss at 7q36.2 was identified resulting in deletion of DPP6 exon 3, and 33 amino acids towards the N-terminal end of the DPP6 protein. These cases evidence digenic involvement in ASD.

The ability of these PTCHD1-mutants to repress Gli2 expression was compared with wild type to determine if there was loss of function in the mutants. NIH10T1/2 fibroblasts were transfected with CMV-empty vector, a Gli-responsive promoter fused to the Luciferase gene (Gli2 pro), β-Gal (normalization) and PTCHD1 mutant expression plasmids. A mild loss of function of at least the E479G and ML336-711 mutants resulted in increased expression of Gli2 compared to wild type.

We claim:

1. A method of detecting a sequence variation of a PTCHD1 gene in an individual, the method comprising: (a) amplifying a PTCHD1 nucleic acid in a biological sample comprising a PTCHD1 nucleic acid obtained from a human; (b) sequencing the PTCHD1 nucleic acid from the biological sample; and (c) detecting the presence of a sequence variant of PTCHD1; wherein the sequence variant of PTCHD1 is a sequence variant of PTCHD1 comprising a C to T mutation at a position corresponding to position 225 of SEQ ID NO: 17.

2. The method of claim 1, wherein the nucleic acid obtained from a human is genomic DNA.

3. The method of claim 1, wherein the amplification comprises amplification with one or more primers selected from the group consisting of SEQ ID NOs: 3-8.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
attcgcagtt ccttcgtctt                                              20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
aaagtggatt gatcggttcc                                              20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gcttgaggac gtgtttctcc                                              20

<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4
ctaggagagg tggcgctct                                               19

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
agcgtgcgcc tcgccct                                                 17

<210> SEQ ID NO 6
<211> LENGTH: 21
<212> TYPE: DNA
```

```
<213> ORGANISM: Artificial
<220> FEATURE:
<223> OTHER INFORMATION: primer

<400> SEQUENCE: 6
tccttgtcca ggaggctggg a                                              21

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
gcgcccgctc tgctcta                                                   17

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
tccttgtcca ggaggctggg a                                              21

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
gaatgtccac cctctccaaa                                                20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
aaggctactc ctggcctttt                                                20

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
ctttgaccca gtagtccctc a                                              21

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
gcacaaaccc cttggtgta                                                 19
```

<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13
tgtgattggg ttttacatat atgagtc                                          27

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
aggtcagatt tgaaggcaca g                                                21

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
aaaaatgccc tggaagtgc                                                   19

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
tgtgtgaatt ctcataacaa ctcct                                            25

<210> SEQ ID NO 17
<211> LENGTH: 5305
<212> TYPE: DNA
<213> ORGANISM: Homo sapiens

<400> SEQUENCE: 17
gctctaggat gctgcggcag gttctgcaca ggggcttgag gacgtgtttc tcccggctcg      60
gccacttcat tgccagtcac cctgtcttct tcgcctcggc gccggtgctc atctccatcc     120
tgctcggcgc cagcttcagc cgctaccagg tcgaggagac cgtggagcac ctgctggcgc     180
cccagcacag cctggccaag atcgagcgca acctcgttaa cagcctcttc ccggtcaacc     240
gctccaagca ccgtctctac tcggacctgc agacccccgg gcgctacggc cgggtcatcg     300
tcacctcctt ccagaaagcc aacatgctgg accagcatca caccgacctg atcttaaagt     360
tgcatgctgc tgtcaccaag atccaggttc caaggcctgg ttttaattac acgtttgccc     420
atatatgtat cctgaataat gataagactt gcatcgtgga tgcatagtg cacgtcctgg     480 aagagctaaa gaatgctcgg gccaccaatc ggaccaattt tgctatcaca tacccaatca     540
ctcacttaaa ggacgggagg gctgtgtaca atgggcacca gcttggggc gtcactgtgc     600 acagcaaaga ccgggtgaaa tctgcagagg ccatccagct cacctactac ctgcagtcaa     660

-continued

```
tcaacagtct caatgacatg gtggctgaga ggtgggagtc cagcttctgc gacactgtca    720
gactgtttca gaaatccaac agcaaagtca aaatgtaccc ttacacgtcc tcctcactga    780
gggaagattt ccagaagacc agccgcgtat cagaacgtta cctggtcacc agcctgattc    840
tggtggttac catggccatc ctgtgttgct ctatgcagga ctgcgtccgc agcaaaccct    900
ggctaggcct gctcggattg gtgaccataa gcctggccac tctcactgca gccgggatca    960
tcaatcttac tggtgggaaa tataattcca ccttcctggg agtccctttc gtcatgctag   1020
gtcatggatt atatgggact tttgaaatgt tatcctcctg gaggaaaact agagaagacc   1080
aacatgttaa agagagaact gcagcagtct atgcagactc catgctctcc ttttctctca   1140
ccactgccat gtacctggtc acctttggca taggggccag ccctttcacg aacattgagg   1200
cagccaggat tttctgctgc aattcctgta ttgcaatctt cttcaactac ctctatgtac   1260
tctcgtttta tggttccagc ctagtgttca ctggctacat agaaaacaat taccagcata   1320
gtatcttctg tagaaaagtc ccaaagcctg aggcattgca ggagaagccg gcatggtaca   1380
ggtttctcct gacggccaga ttcagtgagg acacagctga aggcgaggaa gcgaacactt   1440
acgagagtca cctattggta tgtttcctca aacgctatta ctgtgactgg ataaccaaca   1500
cctatgtcaa gccttttgta gttctctttt accttattta tatttccttt gccttaatgg   1560
gctatctgca ggtcagtgaa gggtcagacc ttagtaacat tgtagcaacc gcgacacaaa   1620
ccattgagta cactactgcc cagcaaaagt acttcagcaa ctacagtcct gtgattgggt   1680
tttacatata tgagtctata gaatactgga cactagtgt ccaagaagat gttctagaat    1740
acaccaaggg gtttgtgcgg atatcctggt ttgagagcta tttaaattac cttcggaaac   1800
tcaatgtatc cactggcttg cctaagaaaa atttcacaga catgttgagg aattcctttc   1860
tgaaagcccc tcaattttca cattttcaag aggacatcat cttctctaaa aaatacaatg   1920
atgaggtcga tgtagtggcc tccagaatgt ttttggtggc caagaccatg gaaacaaaca   1980
gagaagaact ctatgatctc ttggaaaccc tgaggagact ttctgtcacc tccaaggtga   2040
agttcatcgt cttcaatccg tcctttgtat acatggatcg atatgcctcc tctctgggag   2100 ccccctgca caactcctgc atcagtgctt tgttcctgct cttcttctcg gcattcctgg     2160
tggcagattc actgattaac gtctggatca ctctcacagt tgtgtccgtg gagtttggag   2220
tgataggttt catgacatta tggaaagtag aactggactg catttctgtg ctatgcttaa   2280
tttatggaat taattacaca attgacaatt gtgctccaat gttatccaca tttgttctgg   2340
gcaaggattt cacaagaact aaatgggtaa aaaatgccct ggaagtgcat ggggtagcta   2400
ttttacagag ttacctctgc tatattgttg gtctgattcc tcttgcagct gtgccttcaa   2460
atctgacctg tacactgttc aggtgcttgt ttttaatagc atttgtcacc ttcttttcact   2520 gctttgccat tttacctgtg atactgactt tcctgccacc ctctaagaaa aaaggaaag    2580 agaagaaaaa tcctgagaac cgggaggaaa ttgagtgtgt agaaatggta gatatcgata   2640
gtacccgtgt ggttgaccaa attacaacag tgtgataatg tctgcttggc atattttcac   2700
cttaggtcct atcaagacca aagagattat gttaatgaaa caattaaatt caaagttctt   2760
ccctttttta aagataggaa acaggcattg ccaaaaaaaa aaaaaaaaaa aaaggaaag    2820 gacagtgggg agaaatgggc ctggcatatt ttcagtcttt aaaacaaagg agttgttatg   2880
agaattcaca cacacataga cacacacaca cacacacaca cacacacaca cacacacaca   2940
ccctgggaga cctatagtct cttaaactaa gatcaagtag aagaaagctt attaacagc    3000 aggatcctgc cttatccaaa ctgcagatgt tgctggcatt gtgacaaaac ccactgattg   3060
```

```
aaaggtcaac tgccaaggca gaaacacctt taagcattgt tcaaacaata aggcttccag      3120
aacttctgta gagcagtagc tccagtcatg gtctgtggtt tgaggtttta gctgtctcac      3180
ctagctccct aacactgaag gagatacttg tgaaagttct gaccagcaaa agcaagccag      3240
agccttggaa actgatatgt ggtagagtgg ccatcactca tggactaaaa ttgattcacc      3300
gctaaattta cccaggtgaa gcagtttcgt tgtctagaat gaaattatca tattccgcca      3360
ttggtatgcc tttaacattt gtatagtttg gtttgcttaa aacaccttaa aaccaatgac      3420
agctccagca ctgcagaatt ggtgtgattc tactttggaa tagcttgtca cttgtcacca      3480
aatgggtctg ctttattagt tacagctctt ggcaggagga tccagggacc caaaaccaca      3540
gggccaaacc caaataccctg gcatgatgga gcaaaagcag gtgtctactt ggacccagat     3600
atagtgtctc cattttaaca acaacaacaa aatagccagc tggtacagct gtttgcattg      3660
gccctacatg cattttttgc atggatatcc agaaacatct gcccacacaa aactgcgggg     3720
aaaaaaaatg aacactgaaa tagttatttg ctgttgcttc caacttgtag tgccagtctg      3780
cctttgctgt gaaacacacc tgctcagaga cagagagggg aagaagatct ttggtaagtc      3840
taagtcctga cgctgagaag ctttgtaaaa gtgcagggga taaagggcc aaaagggaga      3900 tagatggaaa acactggaaa aagtattcac tgatacaaat ctatcaatga tggcagtcca      3960
attctcttgc taaagtggct gcacctcacc ttgctggtcc cccccacacc ttttttgatg      4020
tccttctgcg tcatcatagc aaggcccttc tgtaaattaa caagcctaga tatttatact      4080
cttgacttcc agtatctaca gaagaatggt tcatagatct aaacagaaat ggtttagatc      4140
taaaaaggct gtatacgttg cccaggcccc tgcatttctt taaatttata aaaatgaagc      4200
taaaacctgg ttacatttga agcaaatatc tacagtattt ttcccttttta gagatgtagc     4260 ttccttagac atctgtagtg gtaagcattt cccaaaagca tcttacctttt ctgaaccttaa    4320 gcagacatac tgtgcagctt acctatcttc tgcagaggag gaaactgaga cctaggagaa      4380
taaagtgact cactcaggtc acaccactaa agggttttca tcatttcagc atacctaaga      4440
cagggcagtc caattttcag tattctcata agatggctat tactcctctc aaaatgcatt      4500
tccaaagtag gaacatagga cttcgttggc cacagggcag acattttttt agtgtctgga      4560
attaaaatgt ttgaggttta ggtttgccat tgtctttcca aaaggccaaa taattcagat      4620
gtaaccacac caagtgcaaa cctgtgcttt ctatttcacg tactgttgtc catacagttc      4680
taaatacatg tgcaggggat tgtagctaat gcattacaca gtcgttcagt cttctctgca      4740
gacacactaa gtgatcatac caacgtgtta tacactcaac tagaagataa taagctttaa      4800
tctgagggca agtacagtcc tgacaaaagg gcaagtttgc ataatagatc ttcgatcaat      4860
tctctctcca aggggcccgc aactaggcta ttattcataa aacacaactg aagagggat      4920 tggttttact gttaaatcat gtgttgctaa atcattttct gaacagtgtg ttctaaatca      4980
gtcattgatt tagtgtcagc cacgtggagc acctcggctt aaagcagctc cacaaaacct      5040
gacacaacac acacaccaat taaatggatt ttgttgagaa tttaatcatt caatttggtc      5100
aaccagaatg acttcctgtg gaactctgtt ttatgacaga taatagtttt ccaacttgat      5160
tgagtctctg tatacccctgg gatattgtat tttttaatga agggcatttt caaacttgtc     5220
aacttctctt ttcagcactt gaaatgaagg cttatggaat tctgactgtg aaatgaattt      5280
ttctattggg aaaaaaaaaa aaaaa                                             5305
```

<210> SEQ ID NO 18

<211> LENGTH: 888
<212> TYPE: PRT
<213> ORGANISM: Homo sapiens

<400> SEQUENCE: 18

```
Met Leu Arg Gln Val Leu His Arg Gly Leu Arg Thr Cys Phe Ser Arg
1               5                   10                  15

Leu Gly His Phe Ile Ala Ser His Pro Val Phe Phe Ala Ser Ala Pro
            20                  25                  30

Val Leu Ile Ser Ile Leu Leu Gly Ala Ser Phe Ser Arg Tyr Gln Val
        35                  40                  45

Glu Glu Ser Val Glu His Leu Leu Ala Pro Gln His Ser Leu Ala Lys
50                  55                  60

Ile Glu Arg Asn Leu Val Asn Ser Leu Phe Pro Val Asn Arg Ser Lys
65                  70                  75                  80

His Arg Leu Tyr Ser Asp Leu Gln Thr Pro Gly Arg Tyr Gly Arg Val
                85                  90                  95

Ile Val Thr Ser Phe Gln Lys Ala Asn Met Leu Asp Gln His His Thr
            100                 105                 110

Asp Leu Ile Leu Lys Leu His Ala Ala Val Thr Lys Ile Gln Val Pro
        115                 120                 125

Arg Pro Gly Phe Asn Tyr Thr Phe Ala His Ile Cys Ile Leu Asn Asn
130                 135                 140

Asp Lys Thr Cys Ile Val Asp Asp Ile Val His Val Leu Glu Glu Leu
145                 150                 155                 160

Lys Asn Ala Arg Ala Thr Asn Arg Thr Asn Phe Ala Ile Thr Tyr Pro
                165                 170                 175

Ile Thr His Leu Lys Asp Gly Arg Ala Val Tyr Asn Gly His Gln Leu
            180                 185                 190

Gly Gly Val Thr Val His Ser Lys Asp Arg Val Lys Ser Ala Glu Ala
        195                 200                 205

Ile Gln Leu Thr Tyr Tyr Leu Gln Ser Ile Asn Ser Leu Asn Asp Met
210                 215                 220

Val Ala Glu Arg Trp Glu Ser Ser Phe Cys Asp Thr Val Arg Leu Phe
225                 230                 235                 240

Gln Lys Ser Asn Ser Lys Val Lys Met Tyr Pro Tyr Thr Ser Ser Ser
                245                 250                 255

Leu Arg Glu Asp Phe Gln Lys Thr Ser Arg Val Ser Glu Arg Tyr Leu
            260                 265                 270

Val Thr Ser Leu Ile Leu Val Val Thr Met Ala Ile Leu Cys Cys Ser
        275                 280                 285

Met Gln Asp Cys Val Arg Ser Lys Pro Trp Leu Gly Leu Leu Gly Leu
290                 295                 300

Val Thr Ile Ser Leu Ala Thr Leu Thr Ala Ala Gly Ile Ile Asn Leu
305                 310                 315                 320

Thr Gly Gly Lys Tyr Asn Ser Thr Phe Leu Gly Val Pro Phe Val Met
                325                 330                 335

Leu Gly His Gly Leu Tyr Gly Thr Phe Glu Met Leu Ser Ser Trp Arg
            340                 345                 350

Lys Thr Arg Glu Asp Gln His Val Lys Glu Arg Thr Ala Ala Val Tyr
        355                 360                 365

Ala Asp Ser Met Leu Ser Phe Ser Leu Thr Thr Ala Met Tyr Leu Val
370                 375                 380

Thr Phe Gly Ile Gly Ala Ser Pro Phe Thr Asn Ile Glu Ala Ala Arg
```

```
              385                 390                 395                 400
        Ile Phe Cys Cys Asn Ser Cys Ile Ala Ile Phe Phe Asn Tyr Leu Tyr
                        405                 410                 415

Val Leu Ser Phe Tyr Gly Ser Ser Leu Val Phe Thr Gly Tyr Ile Glu
                        420                 425                 430

Asn Asn Tyr Gln His Ser Ile Phe Cys Arg Lys Val Pro Lys Pro Glu
                        435                 440                 445

Ala Leu Gln Glu Lys Pro Ala Trp Tyr Arg Phe Leu Leu Thr Ala Arg
        450                 455                 460

Phe Ser Glu Asp Thr Ala Glu Gly Glu Ala Asn Thr Tyr Glu Ser
        465                 470                 475                 480

His Leu Leu Val Cys Phe Leu Lys Arg Tyr Tyr Cys Asp Trp Ile Thr
                        485                 490                 495

Asn Thr Tyr Val Lys Pro Phe Val Val Leu Phe Tyr Leu Ile Tyr Ile
                        500                 505                 510

Ser Phe Ala Leu Met Gly Tyr Leu Gln Val Ser Glu Gly Ser Asp Leu
                        515                 520                 525

Ser Asn Ile Val Ala Thr Ala Thr Gln Thr Ile Glu Tyr Thr Thr Ala
        530                 535                 540

Gln Gln Lys Tyr Phe Ser Asn Tyr Ser Pro Val Ile Gly Phe Tyr Ile
        545                 550                 555                 560

Tyr Glu Ser Ile Glu Tyr Trp Asn Thr Ser Val Gln Glu Asp Val Leu
                        565                 570                 575

Glu Tyr Thr Lys Gly Phe Val Arg Ile Ser Trp Phe Glu Ser Tyr Leu
                        580                 585                 590

Asn Tyr Leu Arg Lys Leu Asn Val Ser Thr Gly Leu Pro Lys Lys Asn
                        595                 600                 605

Phe Thr Asp Met Leu Arg Asn Ser Phe Leu Lys Ala Pro Gln Phe Ser
                        610                 615                 620

His Phe Gln Glu Asp Ile Ile Phe Ser Lys Lys Tyr Asn Asp Glu Val
        625                 630                 635                 640

Asp Val Val Ala Ser Arg Met Phe Leu Val Ala Lys Thr Met Glu Thr
                        645                 650                 655

Asn Arg Glu Glu Leu Tyr Asp Leu Leu Glu Thr Leu Arg Arg Leu Ser
                        660                 665                 670

Val Thr Ser Lys Val Lys Phe Ile Val Phe Asn Pro Ser Phe Val Tyr
                        675                 680                 685

Met Asp Arg Tyr Ala Ser Ser Leu Gly Ala Pro Leu His Asn Ser Cys
        690                 695                 700

Ile Ser Ala Leu Phe Leu Leu Phe Phe Ser Ala Phe Leu Val Ala Asp
        705                 710                 715                 720

Ser Leu Ile Asn Val Trp Ile Thr Leu Thr Val Val Ser Val Glu Phe
                        725                 730                 735

Gly Val Ile Gly Phe Met Thr Leu Trp Lys Val Glu Leu Asp Cys Ile
                        740                 745                 750

Ser Val Leu Cys Leu Ile Tyr Gly Ile Asn Tyr Thr Ile Asp Asn Cys
                        755                 760                 765

Ala Pro Met Leu Ser Thr Phe Val Leu Gly Lys Asp Phe Thr Arg Thr
        770                 775                 780

Lys Trp Val Lys Asn Ala Leu Glu Val His Gly Val Ala Ile Leu Gln
        785                 790                 795                 800

Ser Tyr Leu Cys Tyr Ile Val Gly Leu Ile Pro Leu Ala Ala Val Pro
                        805                 810                 815
```

```
Ser Asn Leu Thr Cys Thr Leu Phe Arg Cys Leu Phe Leu Ile Ala Phe
            820             825             830

Val Thr Phe Phe His Cys Phe Ala Ile Leu Pro Val Ile Leu Thr Phe
            835             840             845

Leu Pro Pro Ser Lys Lys Arg Lys Glu Lys Lys Asn Pro Glu Asn
850             855             860

Arg Glu Glu Ile Glu Cys Val Glu Met Val Asp Ile Asp Ser Thr Arg
865             870             875             880

Val Val Asp Gln Ile Thr Thr Val
            885
```